United States Patent
Sharei et al.

(10) Patent No.: US 11,299,698 B2
(45) Date of Patent: Apr. 12, 2022

(54) DELIVERY OF MATERIALS TO ANUCLEATE CELLS

(71) Applicant: Massachusetts Institute of Technology, Cambridge, MA (US)

(72) Inventors: Armon R. Sharei, Watertown, MA (US); Klavs F. Jensen, Lexington, MA (US); James Robbins Abshire, Cambridge, MA (US); Jacquin Clarence Niles, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 141 days.

(21) Appl. No.: 15/865,901

(22) Filed: Jan. 9, 2018

(65) Prior Publication Data

US 2018/0201889 A1   Jul. 19, 2018

Related U.S. Application Data

(63) Continuation of application No. PCT/US2016/041653, filed on Jul. 8, 2016.

(60) Provisional application No. 62/190,677, filed on Jul. 9, 2015.

(51) Int. Cl.
| | |
|---|---|
| *C12N 15/87* | (2006.01) |
| *C12N 5/078* | (2010.01) |
| *A61K 35/18* | (2015.01) |
| *C12M 3/06* | (2006.01) |
| *C12M 1/42* | (2006.01) |

(52) U.S. Cl.
CPC .............. *C12M 23/16* (2013.01); *A61K 35/18* (2013.01); *C12M 35/04* (2013.01); *C12N 5/0641* (2013.01); *C12N 5/0644* (2013.01); *C12N 15/87* (2013.01); *C12N 2521/00* (2013.01); *C12N 2527/00* (2013.01)

(58) Field of Classification Search
None
See application file for complete search history.

(56) References Cited

U.S. PATENT DOCUMENTS

| | | |
|---|---|---|
| 4,055,799 A | 10/1977 | Coster |
| 4,376,634 A | 3/1983 | Prior et al. |
| 4,835,457 A | 5/1989 | Hanss |
| 5,023,054 A | 6/1991 | Sato et al. |
| 5,643,577 A | 7/1997 | Pang et al. |
| 5,658,892 A | 8/1997 | Flotte et al. |
| 5,842,787 A | 12/1998 | Kopf-Sill et al. |
| 5,951,976 A | 9/1999 | Segal |
| 6,133,503 A | 10/2000 | Scheffler |
| 6,156,181 A | 12/2000 | Parce et al. |
| 6,186,660 B1 | 2/2001 | Kopf-Sill et al. |
| 6,218,166 B1 | 4/2001 | Ravindranath et al. |
| 6,410,329 B1 | 6/2002 | Hansen et al. |
| 6,461,867 B1 | 10/2002 | Cai et al. |
| 6,562,616 B1 | 5/2003 | Toner et al. |
| 7,109,034 B2 | 9/2006 | Ormar et al. |
| 7,704,743 B2 | 4/2010 | Fedorov et al. |
| 7,993,821 B2 | 8/2011 | Chiu et al. |
| 8,211,656 B2 | 7/2012 | Hyde et al. |
| 8,669,044 B2 | 3/2014 | Chiu et al. |
| 8,679,751 B2 | 3/2014 | Huang |
| 8,697,359 B1 | 4/2014 | Zhang |
| 8,844,570 B2 | 9/2014 | Glick et al. |
| 9,005,579 B2 | 4/2015 | Nowinski et al. |
| 9,017,991 B2 | 4/2015 | Diefenbach |
| 9,157,550 B2 | 10/2015 | Wheeler et al. |
| 9,255,245 B2 | 2/2016 | Bernick et al. |
| 9,364,504 B2 | 6/2016 | Godfrin et al. |
| 9,458,489 B2 | 10/2016 | Lim et al. |
| 9,950,049 B2 | 4/2018 | Godfrin et al. |

(Continued)

FOREIGN PATENT DOCUMENTS

| | | |
|---|---|---|
| CN | 101031339 A | 9/2007 |
| CN | 101031641 A | 9/2007 |

(Continued)

OTHER PUBLICATIONS

Magnani et al. "Erythrocyte engineering for drug delivery and targeting." Biotechnology and Applied Biochemistry 28.1 (1998): 1-6. (Year: 1998).*
Hirlekar et al. "Drug loaded erythrocytes: as novel drug delivery system." Current pharmaceutical design 14.1 (2008): 63-70. (Year: 2008).*
Getasew et al. "Advance Malaria treatment in pregnant women." European Journal of Clinical Pharmacy 19.5 (2017): 325-34. (Year: 2017).*
De Clercq et al. "Antiviral agents active against human herpesviruses HHV-6, HHV-7 and HHV-8." Reviews in Medical Virology 11.6 (2001): 381-395. (Year: 2001).*
Adamo, Andrea et al., "Microfluidics-Based Assessment of Cell Deformability," Analytical Chemistry (Aug. 7, 2012), vol. 84, No. 15, pp. 6438-6443.

(Continued)

*Primary Examiner* — Emily A Cordas
(74) *Attorney, Agent, or Firm* — Wolf, Greenfield & Sacks, P.C.

(57) ABSTRACT

The current subject matter includes methods, systems, articles, and techniques to deliver material to anucleate cells, such as red blood cells. Using a rapid deformation based microfluidic system, loading of red blood cells with macromolecules of different sizes has been shown. Although delivery to some mammalian cells, such as cancer cell lines and fibroblasts had been previously demonstrated using this technique, those designs were incompatible with RBCs that have dramatically different physical properties. Through the use of smaller constriction sizes, high speeds and different buffers successful delivery to red blood cells can be achieved. By enabling robust delivery to red blood cells in a simple, scalable manner, the current subject matter can be implemented in a diversity of applications that deliver material to study red blood cell diseases and/or use red blood cells as a therapeutic platform. Related apparatus, systems, techniques, and articles are also described.

27 Claims, 6 Drawing Sheets

(56) References Cited

U.S. PATENT DOCUMENTS

| | | | |
|---|---|---|---|
| 10,124,336 B2 | 11/2018 | Sharei et al. | |
| 10,526,573 B2 | 1/2020 | Ding et al. | |
| 10,696,944 B2 | 6/2020 | Sharei et al. | |
| 10,870,112 B2 | 12/2020 | Sharei et al. | |
| 11,111,472 B2 | 9/2021 | Sharei et al. | |
| 11,125,739 B2 | 9/2021 | Sharei et al. | |
| 2003/0133922 A1 | 7/2003 | Kasha, Jr. | |
| 2004/0176282 A1 | 9/2004 | Dalby et al. | |
| 2004/197898 A1 | 10/2004 | Nakatani et al. | |
| 2005/0026283 A1 | 2/2005 | Ormar et al. | |
| 2006/0134067 A1 | 6/2006 | Liu et al. | |
| 2006/0134772 A1 | 6/2006 | Miles et al. | |
| 2006/0223185 A1 | 10/2006 | Fedorov et al. | |
| 2007/0243523 A1 | 10/2007 | Ionescu-Zanetti et al. | |
| 2007/0249038 A1 | 10/2007 | Adamo et al. | |
| 2008/0026465 A1 | 1/2008 | Nakata | |
| 2008/0241844 A1 | 10/2008 | Kellogg | |
| 2008/0311140 A1 | 12/2008 | Lee et al. | |
| 2008/0318324 A1 | 12/2008 | Chiu et al. | |
| 2009/0209039 A1 | 9/2009 | Adamo et al. | |
| 2009/0280518 A1 | 11/2009 | Adamo et al. | |
| 2010/0203068 A1 | 8/2010 | Betz et al. | |
| 2010/0249621 A1 | 9/2010 | Ichitani | |
| 2010/0323388 A1 | 12/2010 | Chiu et al. | |
| 2011/0014616 A1 | 1/2011 | Holmes et al. | |
| 2011/0030808 A1 | 2/2011 | Chiou et al. | |
| 2011/0091973 A1 | 4/2011 | Glaser | |
| 2011/0300205 A1 | 12/2011 | Geall et al. | |
| 2012/0064505 A1 | 3/2012 | Suresh et al. | |
| 2012/0107925 A1 | 5/2012 | Li et al. | |
| 2012/0207745 A1 | 8/2012 | Godfrin et al. | |
| 2012/0222143 A1 | 8/2012 | Fahrenkrug et al. | |
| 2013/0023051 A1 | 1/2013 | Bundock et al. | |
| 2013/0045211 A1 | 2/2013 | Nowinski et al. | |
| 2013/0065314 A1 | 3/2013 | Macmillan | |
| 2014/0011226 A1 | 1/2014 | Bernick et al. | |
| 2014/0273229 A1 | 9/2014 | Meacham et al. | |
| 2014/0287509 A1 | 9/2014 | Sharei et al. | |
| 2015/0184127 A1 | 7/2015 | White et al. | |
| 2015/0196913 A1 | 7/2015 | Liu | |
| 2016/0017340 A1 | 1/2016 | Wu et al. | |
| 2016/0193605 A1 | 7/2016 | Sharei et al. | |
| 2016/0199837 A1 | 7/2016 | Breinlinger et al. | |
| 2017/0020926 A1 | 1/2017 | Mata-Fink et al. | |
| 2017/0326213 A1 | 11/2017 | Jajosky et al. | |
| 2018/0003696 A1 | 1/2018 | Sharei et al. | |
| 2018/0016539 A1 | 1/2018 | Ding et al. | |
| 2018/0085402 A1 | 3/2018 | Kahvejian et al. | |
| 2018/0142198 A1 | 5/2018 | Sharei et al. | |
| 2018/0245089 A1 | 8/2018 | Sharei et al. | |
| 2019/0017072 A1 | 1/2019 | Ditommaso et al. | |
| 2019/0030536 A1 | 1/2019 | Sharei et al. | |
| 2019/0093073 A1 | 3/2019 | Sharei et al. | |
| 2019/0111082 A1 | 4/2019 | Gilbert et al. | |
| 2019/0382796 A1 | 12/2019 | Gilbert et al. | |
| 2020/0277566 A1 | 9/2020 | Sharei et al. | |
| 2021/0170411 A1 | 6/2021 | Sharei et al. | |

FOREIGN PATENT DOCUMENTS

| | | | | |
|---|---|---|---|---|
| CN | 106244543 A | 12/2016 | | |
| EP | 882448 A1 | 12/1998 | | |
| EP | 1225228 A2 | 7/2002 | | |
| EP | 2169070 A1 | 3/2010 | | |
| JP | H01196566 A | 8/1989 | | |
| JP | H03257366 A | 11/1991 | | |
| JP | 2010-02582 A | 2/2010 | | |
| JP | 2010-025852 A | 2/2010 | | |
| JP | 2011-163830 A | 8/2011 | | |
| JP | 2013-536848 A | 9/2013 | | |
| JP | 6235085 B2 | 11/2017 | | |
| KR | 100760309 B1 | 10/2007 | | |
| KR | 100891487 B1 | 4/2009 | | |
| KR | 20110009422 A | 1/2011 | | |
| KR | 2014-0115560 A | 10/2014 | | |
| KR | 20140134524 A | 11/2014 | | |
| WO | WO 85/00748 A1 | 2/1985 | | |
| WO | WO 97/20570 A1 | 6/1997 | | |
| WO | WO 00/07630 A1 | 2/2000 | | |
| WO | WO 02/067863 A2 | 9/2002 | | |
| WO | WO 03/020039 A1 | 3/2003 | | |
| WO | WO 2004/001424 A1 | 12/2003 | | |
| WO | WO 2006/010521 A1 | 2/2006 | | |
| WO | WO 2006/095330 A2 | 9/2006 | | |
| WO | WO 2006/0105251 A2 | 10/2006 | | |
| WO | WO 2007/067032 A1 | 6/2007 | | |
| WO | WO 2007/097934 A2 | 8/2007 | | |
| WO | WO 2008/021465 A2 | 2/2008 | | |
| WO | WO 2008/0214565 A2 | 2/2008 | | |
| WO | WO 2009/056332 A1 | 5/2009 | | |
| WO | WO 2010/016800 A1 | 2/2010 | | |
| WO | WO 2010/077290 A1 | 7/2010 | | |
| WO | WO 2010/105135 A1 | 9/2010 | | |
| WO | WO 2010/129671 A2 | 11/2010 | | |
| WO | WO 2010/145849 A2 | 12/2010 | | |
| WO | WO 2011/051346 A1 | 5/2011 | | |
| WO | WO 2011/119492 A2 | 9/2011 | | |
| WO | WO-2011119492 A2 | * | 9/2011 | ........ B01L 3/502746 |
| WO | WO 2012/069568 A2 | 5/2012 | | |
| WO | WO 2012/097450 A1 | 7/2012 | | |
| WO | WO 2012/106536 A2 | 8/2012 | | |
| WO | WO 2012/118799 A2 | 9/2012 | | |
| WO | WO 2012/162779 A1 | 12/2012 | | |
| WO | WO 2013/059343 A1 | 4/2013 | | |
| WO | WO 2013/185032 A1 | 12/2013 | | |
| WO | WO 2014/065596 A1 | 5/2014 | | |
| WO | WO 2014/106629 A1 | 7/2014 | | |
| WO | WO 2014/106631 A1 | 7/2014 | | |
| WO | WO 2014/120956 A1 | 8/2014 | | |
| WO | WO 2014/165707 A2 | 10/2014 | | |
| WO | WO 2015/023982 A1 | 2/2015 | | |
| WO | WO 2015/061458 A1 | 4/2015 | | |
| WO | WO 2015/153102 A1 | 10/2015 | | |
| WO | WO 2015/161276 A2 | 10/2015 | | |
| WO | WO 2016/003485 A1 | 1/2016 | | |
| WO | WO 2016/070136 A1 | 5/2016 | | |
| WO | WO 2016/077761 A1 | 5/2016 | | |
| WO | WO 2016/109864 A1 | 7/2016 | | |
| WO | WO 2016/115179 A1 | 7/2016 | | |
| WO | WO 2016/183482 A1 | 11/2016 | | |
| WO | WO 2017/005700 A1 | 1/2017 | | |
| WO | WO 2017/008063 A1 | 1/2017 | | |
| WO | WO 2017/041050 A1 | 3/2017 | | |
| WO | WO 2017/041051 A1 | 3/2017 | | |
| WO | WO 2017/106899 A2 | 6/2017 | | |
| WO | WO 2017/123644 A1 | 7/2017 | | |
| WO | WO 2017/123646 A1 | 7/2017 | | |
| WO | WO 2017/123663 A1 | 7/2017 | | |
| WO | WO 2017/192785 A1 | 11/2017 | | |
| WO | WO 2017/192786 A1 | 11/2017 | | |
| WO | WO 2018/089497 A1 | 5/2018 | | |

OTHER PUBLICATIONS

ATCC Thawing, Propagating, and Cryopreserving Protocol, NCI-PBCF-HTB81 (DU 145), Prostate Carcinoma (ATCC® htb-81), Version 1.6, 2012, 23 pages.

Augustsson et al. "Microfluidic, Label-Free Enrichment of Prostate Cancer Cells in Blood Based on Acoustophoresis," Analytical Chemistry, Aug. 28, 2012 (Aug. 28, 2012), vol. 84, No. 18, pp. 7954-7962.

BD Bioscience FITC-labeled anti-CD45 antibody, 2 pages.

BD Bioscience PE-labeled anti-EpCAM antibody, 2 pages.

Boohaker, et al., "The Use of Therapeutic Peptides to Target and to Kill Cancer Cells," Curr. Med. Chem., 19(22), 26 pages, 2012.

Cancer Facts & Figures 2012. Published by the American Cancer Society in Atlanta, 68 pages.

Certificate of Grant dated Jan. 11, 2018 for Chinese Application No. 201280060689.6.

Cross et al., "Nanomechanical analysis of cells from cancer patients," Nature Nanotechnology (Dec. 2007), vol. 2, pp. 780-783.

Downs, C. A. et al. (May 14, 2011). "Cell Culture Models Using Rat Primary Alveolar type 1 Cells", Pulmonary Pharm. & Therapeutics 24(5)577-586.

(56) References Cited

OTHER PUBLICATIONS

Eixarch, H. et al. "Tolerance induction in experimental autoimmune encephalomyelitis using non-myeloablative hematopoietic gene therapy with autoantigen." Molecular Therapy 17.5 (2009): 897-905.
Esposito et al., "Intraerythrocytic administration of a synthetic Plasmodium antigen elicits antibody response in mice, without carrier molecules or adjuvants," International Journal of Parasitology, vol. 20, No. 8, pp. 1109-1111 (1990).
European Search Opinion dated Apr. 30, 2015 from European Application No. 12 841 329, 2 pages.
Examination Report No. 1 dated Dec. 1, 2016 from Australian Application No. 2012326203, 10 pages.
Examination Report No. 2 dated Jul. 26, 2017 from Australian Application No. 2012326203, 6 pages.
Extended European Search Report for EP 14836593.5, dated Feb. 23, 2017, 9 pages.
Gasteiger, et al., "Protein Identification and Analysis Tools on the ExPASy Server," The Proteomics Handbook, Chapter 52, pp. 571-607, 2005.
Griesbeck et al., "Sex Differences in Plasmacytoid Dendritic Cell Levels of IRF5 Drive higher IFN-alpha production in Women," The Journal of Immunology (Dec. 2015), vol. 195(11):5327-5336.
Hallow et al., "Shear-Induced Intracellular Loading of Cells With Molecules by Controlled Microfluidics," Biotechnology and Bioengineering (2008), vol. 99(4):846-854.
Han, X. et al., "CRISPR-Cas9 delivery to hard-to-transfect cells via membrane deformation," Sci. Adv., Aug. 14, 2015, e1500454, 8 pages.
Hillerdal et al., "Systemic treatment with CAR-engineered T cells against PSCA delays subcutaneous tumor growth and prolongs survival of mice," BMC Cancer (Jan. 18, 2014), vol. 14, No. 30, pp. 1-9.
Hoeppener et al., "Immunomagnetic Separation Technologies," In: Ignatiadis M., Soritiou C., Pantel K. (eds.), Minimal Residual Disease and Circulating Tumor Cells in Breast Cancer. Recent Results in Cancer Research, vol. 195, pp. 43-58 (2012).
Hoskin, et al., "Studies on anticancer activitied of antimicrobial peptides," Biochimica et Biophysica Acta, v.1778, pp. 357-375, 2008.
Hosokawa, et al., "Size-Selective Microacvity Array for Rapid and Efficient Detection of Circulation Tumor Cells," Anal. Chem, 85:6629-6635, 2010.
Howarth, M. et al. (May 2008). "Monovalent, Reduced-Size Quantum Dots For Imaging Receptors On Living Cells," Nature Methods 5(5):397-399.
International Preliminary Report on Patentability dated Feb. 16, 2016 from International Application No. PCT/US2014/051343.
International Preliminary Report on Patentability, PCT/US2012/060646, dated Apr. 22, 2014, 7 pages.
International Preliminary Report on Pattentability, PCT/US2015/058489, dated May 2, 2017, 12 pages.
International Preliminary Report on Pattentability, PCT/US2015/060689, dated May 16, 2017, 10 pages.
International Search Report and Written Opinion dated Jan. 3, 2017 from International Application No. PCT/US2016/050287, 13 pages.
International Search Report and Written Opinion dated Jan. 12, 2016 from International Application No. PCT/US2016/050288, 11 pages.
International Search Report and Written Opinion dated Feb. 1, 2016 from International Application No. PCT/US15/60689.
International Search Report and Written Opinion dated Feb. 25, 2013 from International Application No. PCT/US12/060646.
International Search Report and Written Opinion dated Mar. 11, 2016 from International Application No. PCT/US15/584489.
International Search Report and Written Opinion dated Mar. 21, 2016 from International Application No. PCT/US2016/013113.
International Search Report and Written Opinion dated Dec. 18, 2014 from International Application No. PCT/US2014/051343.
International Search Report and Written Opinion dated Jul. 21, 2017 from International Application No. PCT/US2017/030933, 20 pages.
International Search Report and Written Opinion dated Sep. 19, 2017 from International Application No. PCT/US2017/030932, 18 pages.
Janeway Ca Jr, et al., "The structure of a typical antibody molecule," Immunobiology: The Immune System in Heath and Disease, 5th edition (2001), 5 pages.
Kim, D., et al., "Microengineered Platforms for Cell Mechanobiology," Annual Review of Biomedical Engineering, 2009, vol. 11, pp. 203-233.
Lee et al., "Nonendocytic delivery of functional engineered nanoparticles into the cytoplasm of live cells using a novel, high-throughput microfluidic device," Nano Letters (2012), vol. 12, pp. 6322-6327.
Lin et al., "Highly selective biomechanical separation of cancer cells from leukocytes using microfluidic and hydrodynamic concentrator," Biomicrofluidics (Jun. 26, 2013), vol. 7, No. 3, pp. 34114-1-11.
Liu et al., "Molecular imaging in tracking tumor-specific cytotoxic T lymphocytes (CTLs)," Theranostics (Jul. 28, 2014), vol. 4, No. 10, pp. 990-1001.
Liu et al., "Spatially selective reagent delivery into cancer cells using a two-layer microfluidic culture system," Analytica Chimica Acta (Sep. 1, 2012), vol. 743, pp. 125-130.
Liu, W. et al. (Jan. 20, 2010). "Compact Biocompatible Quantum Dots Via RAFT-Mediated Synthesis of Imidazole-Based Random Copolymer Ligand," JACS 132(2):472-483.
Mattews, B.D., et al., "Cellular adaptation to mechanical stress: role of integrins, Rho, cytoskeletal tension and mechanosensitive ion channels," Journal of Cell Science, vol. 119, pp. 508-518, 2006.
Milo, R. "What is the total number of protein molecules per cell volume? A call to rethink some published values." Bioessays 35.12 (2013): 1050-1055.
Murphy, J. S. et al. (Sep. 1, 1956, e-pub May 2004). "Measurement of Wall Shearing Stress in the Boundary Layer by Means of an Evaporating Liquid Film," Journal of Applied Physics 27(9):1097-1103.
Notice of Grant dated Jan. 11, 2018 for Chinese Patent Application No. 201280060689.6.
Office Action dated Dec. 1, 2016 from Chinese Application No. 201280060689.6, 4 pages.
Office Action dated Dec. 17, 2014 from Chinese Office Action No. 201280060689.6, 9 pages.
Office Action dated Jul. 7, 2016 from Japanese Application No. 2014-537184, 7 pages.
Office Action dated Jun. 14, 2016 from European Application No. 12 841 329, 4 pages.
Office Action dated Jun. 23, 2017 from Chinese Application No. 201280060689.6, 4 pages.
Office Action dated May 13, 2016 from Chinese Application No. 201280060689.6, 4 pages.
Office Action dated Oct. 11, 2017 from European Application No. 12 841 329, 4 pages.
Office Action dated Sep. 6, 2015 from Chinese Office Action No. 201280060689.6, 8 pages.
Office Action dated Aug. 15, 2017 from U.S. Appl. No. 14/912,001, 32 pages.
Office Action dated Feb. 24, 2017 from U.S. Appl. No. 14/352,354, 11 pages.
Office Action dated Jul. 27, 2016 from U.S. Appl. No. 14/352,354, 9 pages.
Office Action dated Jul. 5, 2017 from Chinese Application No. 201480056295.2, 13 pages.
Office Action dated Jul. 7, 2016 from Japanese Application No. 2014-537184, 14 pages.
Office Action dated Mar. 16, 2017 from U.S. Appl. No. 14/912,001, 29 pages.
Office Action dated Mar. 23, 2017 from Russian Application No. 2014119926/10(031699), 10 pages.
Office Action dated May 1, 2017 from Japanese Application No. 2014-537184, 13 pages.
Office Action dated Oct. 26, 2016 from Russian Application No. 2014119926/10(031699), 10 pages.

(56) References Cited

OTHER PUBLICATIONS

Polvani et al., "Murine Red Blood Cells as Efficient Carriers of Three Bacterial Antigens for the Production of Specific and Neutralizing Antibodies," Biotechnology and Applied Biochemistry, vol. 14, pp. 347-356 (1991).
Ravilla et al., "Erythrocytes as Carrier for Drugs, Enzymes and Peptides," Journal of Applied Pharmaceutical Science, vol. 2, No. 2, pp. 166-176 (2012).
Rutella et al., "Tolerogenic dendritic cells: cytokine modulation comes of age," Blood, vol. 108, No. 5, pp. 1435-1440 (2006).
Sharei et al, "Ex vivo Cytosolic Delivery of Functional Macromolecules to Immune Cells," (Apr. 13, 2015), PLoS One, vol. 10, No. 4, 12 pp. e0118803.
Sharei et al., "A vector-free microfluidic platform for intracellular delivery," Proc. Natl. Acad. Sci. USA (Feb. 5, 2013), vol. 110, No. 6, pp. 2082-2087.
Sharei et al., "Cell Squeezing as a Robust, Microfluidic Intracellular Delivery Platform," Journal of Visualized Experiments (Nov. 7, 2013), No. 81, 9 pages.
Sharei et al., "Microfluidic Cell Deformation As a Robust, Vector-Free Method for Cystosolic Delivery of Macromolecules 2012 Annual Meeting," (Jan. 1, 2012), 3 pages.
Sharei et al., "Plasma membrane recovery kinetics of a microfluidic intracellular delivery platform," Integrative Biology (2014), vol. 6, pp. 470-475.
Shelby et al., "A microfluidic model for single-cell capillary obstruction by Plasmodium falciparum infected erythrocytes," (Dec. 9, 2003), Proc. Nat. Acad. Sci., vol. 100, No. 25, pp. 14618-14622.
Steinman et al., "Tolerogenic dendritic cells," Annual Review of Immunology, vol. 21, pp. 685-711 (2003).
Stewart et al., "In vitro and ex vivo strategies for intracellular delivery," Nature, vol. 538, No. 7624, pp. 183-192 (2016).
Supplementary European Search Report dated Apr. 30, 2015 from European Application No. 12 841 329, 3 pp.
Swaminathan, et al., "Mechanical Stiffness Grades Metastatic Potential in Patient Tumor Cells and in Cancer Cell Lines," Cancer Research, 71(15):5075-5080, 2011.
Szeto et al., "Microfluidic squeezing for intracellular antigen loading in polyclonal B-cells as cellular vaccines," Scientific Reports, vol. 5, 10276 (May 2015), 13 pages.
Third-Party Submission mailed Oct. 23, 2015 from U.S. Appl. No. 14/352,354, 21 pages.
Williams, A.R. et al. (Nov. 5, 1999). "Filtroporation: A Simple, Reliable Technique for Transfection and Macromolecular Loading of Cells", Biotechnology and Bioengineering 65(3)341-346.
Zarnitsyn et al., "Electrosonic ejector microarray for drug and gene delivery," Biomed Microdevices (2008) 10:299-308.
Extended European Search Report for EP App. No. 15859824.3 dated Sep. 11, 2018.
Extended European Search Report for EP App. No. 15855640.7 dated Sep. 5, 2018.
Ditommaso et al., Cell engineering with microfluidic squeezing preserves functionality of primary immune cells in vivo. PNAS. Oct. 2018;115(46):E10907-14.
Gossett et al., Hydrodynamic stretching of single cells for large population mechanical phenotyping. PNAS. May 2012;109(20):7630-5.
Nic an Tsaoir et al., Scalable Antibody Production from CHO Cell Line of Choice Using Flow Electroporation. MaxCyte. Jun. 2016. 1 page.
Sharei et al., "A vector-free microfluidic platform for intracellular delivery," Proc. Natl. Acad. Sci. USA (Feb. 5, 2013), vol. 110, No. 6, Supporting Information. 10 pages.
Stevenson, D. J. et al., "Single cell optical transfection," J. R. Soc. Interface, vol. 7, 863-871 (2010).
Weaver et al., A brief overview of electroporation pulse strength-duration space: A region where additional intracellular effects are expected. Bioelectrochemistry. Oct. 2012;87:236-43.
Extended European Search Report for EP App. No. 16822078.8 dated Jan. 30, 2019.
International Search Report and Written Opinion for PCT/US2016/041653 dated Oct. 4, 2016.
International Preliminary Report on Patentability for PCT/US2016/041653 dated Jan. 18, 2018 (Chapter I).
Extended European Search Report for EP App. No. 16737769.6 dated May 3, 2018.
International Preliminary Report on Patentability for PCT/US2016/013113 dated Jul. 27, 2017 (Chapter I).
Partial Supplementary European Search Report for EP App. No. 15859824.3 dated Jun. 11, 2018.
Partial Supplementary European Search Report for EP App. No. 15855640.7 dated May 30, 2018.
Banz, A. et al., "Tumor Growth Control Using Red Blood Cells as the Antigen Delivery System and Poly(I:C)," J Immunother 2012, 35(5), pp. 409-417.
Chaw et al. Multi-step microfluidic device for studying cancer metastasis. Lab on a Chip (2007), v7, p. 1041-1047.
Cremel, L. et al., "Innovative approach in Pompe disease therapy: Induction of immune tolerance by antigen-encapsulated red blood cells," Int J Pharm. Aug. 1, 2015;491(1-2), pp. 69-77.
Cremel, L. et al., "Red blood cells as innovative antigen carrier to induce specific immune tolerance," Int J Pharm. Feb. 25, 2013;443(1-2), pp. 39-49.
Ding, X. et al., "High-throughput nuclear delivery and rapid expression of DNA via mechanical and electrical cell-membrane disruption," Nature Biomedical Engineering (2017), vol. 1, No. 3, 7 pages.
Favretto, M. E. et al., "Human erythrocytes as drug carriers: Loading efficiency and side effects of hypotonic dialysis, chlorpromazine treatment and fusion with liposomes," Journal of Controlled Release 2013; 170: 343-351.
Grimm, A. J. et al., "Memory of tolerance and induction of regulatory T cells by erythrocyte-targeted antigens," Sci Rep. Oct. 29, 2015;5:15907, 11 pages.
Kiani et al., Cas9 gRNA engineering for genome editing, activation and repression. Nature Methods. 2015;12:1051-4.
Li, J. et al., "Microfluidic-Enabled Intracellular Delivery of Membrane Impermeable Inhibitors to Study Target Engagement in Human Primary Cells," ACS Chemical Biology 2017, vol. 12, No. 12, pp. 2970-2974.
Lorentz, K. M. et al., "Engineered binding to erythrocytes induces immunological tolerance to E. coli asparaginase," Sci Adv. Jul. 17, 2015;1(6):e1500112, 11 pages.
Mali, P. et al., "RNA-guided human Genome Engineering via Cas9," Science (2013), vol. 339, No. 6121, pp. 823-826.
Maratou et al., Glucose transporter expression on the plasma membrane of resting and activated while blood cells. European Journal of Clinical Investigation. 2007;37:282-90.
Rossi, L. et al., "Erythrocyte-mediated delivery of phenylalanine ammonia lyase for the treatment of phenylketonuria in BTBR-Pah.sup.enu2 mice," Journal of Controlled Release 194;37-44 (2014).
Rughetti, A. et al., "Transfected human dendritic cells to induce antitumor immunity," Gene Therapy, vol. 7, pp. 1458-1466 (2000).
Stevenson, D. J. et al., "Single cell optical transfection," IEEE Transactions on Ultrasonics, Ferroelectrics and Frequency Control, vol. 53, No. 1, 863-871 (2010).
Tlaxca, J. L. et al., "Analysis of in vitro Transfection by Sonoporation Using Cationic and Neutral Microbubbles," Ultrasound in Medicine and Biology, vol. 36, No. 11, 1907-1918 (2010).
Wright et al., Rational design of a split-Cas9 enzyme complex. PNAS. Mar. 2015;112(10):2984-9.
Yin et al., "Delivery technologies for genome editing," Nature Reviews (2017), vol. 16, No. 6, pp. 387-399.
Zdobnova et al., Self-Assembling Complexes of Quantum Dots and scFv Antibodies for Cancer Cell Targeting and Imaging. PLoS One. 2012;7(10):e48248. 8 pages.
Extended European Search Report dated Nov. 21, 2019 for Application No. EP 19187758.8.
Fagerlund et al., The Cpf1 CRISPR-Cas protein expands genome-editing tools. Genome Biol. Nov. 17, 2015;16:251. doi: 10.1186/s13059-015-0824-9.
[No Author Listed], SQZ Biotech and AskBio Announce Research Collaboration to Create Immune Tolerization Products for AAV Gene Therapies. AskBio. Press Release. Nov. 7, 2019. 3 pages.

(56) References Cited

OTHER PUBLICATIONS

[No Author Listed], SQZ Biotech Announces Pricing of Initial Public Offering. SQZ Biotech. Press Release. Oct. 29, 2020. 2 pages.

[No Author Listed], SQZ Biotech Closes $65 Million Series D Financing. SQZ Biotech. Press Release. May 18, 2020. 2 pages.

[No Author Listed], SQZ Biotechnologies Presents Preclinical Data for their SQZ Tolerizing Antigen Carrier Platform in Antigen-Specific Immune Tolerance (ASIT) Digital Summit Invited Talk. SQZ Biotech. Press Release. Jan. 27, 2021. 4 pages.

Alberts et al., Chapter 11: Ion Channels and the Electrical Properties of Membranes. Molecular Biology of the Cell, $4^{th}$ Ed. New York: Garland Science. 2002. 20 pages.

Azarikia et al., Stabilization of biopolymer microgels formed by electrostatic complexation: Influence of enzyme (laccase) cross-linking on pH, thermal, and mechanical stability. Food Res Int. Dec. 2015;78:18-26. doi: 10.1016/j.foodres.2015.11.013. Epub Nov. 21, 2015.

Blagovic et al., 165 Activating antigen carriers generated with microfluidics cell squeezing drive effective anti-tumor responses. JITC. Dec. 2020;8:A98-9. doi: 10.1136/jitc-2020-SITC2020.0165.

Bosilkovski, This MIT PhD Just Raised $65 Million For His Clinical Stage Cell Therapy Company. Forbes. May 21, 2020. https://www.forbes.com/sites/igorbosilkovski/2020/05/21/meet-the-mit-phd-who-just-raised-65-million-for-his-clinical-stage-cell-therapy-company/?sh=1e9a48af9809 [last accessed Jan. 28, 2021]. 3 pages.

Chen et al., Patch clamping on plane glass-fabrication of hourglass aperture and high-yield ion channel recording. Lab Chip. Aug. 21, 2009;9(16):2370-80. Epub May 14, 2009. https://doi.org/10.1039/b901025d.

Escoffre et al., What is (still not) known of the mechanism by which electroporation mediates gene transfer and expression in cells and tissues. Mol Biotechnol. Mar. 2009;41(3):286-95. doi: 10.1007/s12033-008-9121-0. Epub Nov. 18, 2008.

Gilbert, T-cell-inducing vaccines—what's the future. Immunology. Jan. 2012;135(1):19-26. doi: 10.1111/j.1365-2567.2011.03517.x.

Golzio et al., Direct visualization at the single-cell level of electrically mediated gene delivery. Proc Natl Acad Sci U S A. Feb. 5, 2002;99(3):1292-7. doi: 10.1073/pnas.022646499. Epub Jan. 29, 2002.

Jiang, The immunopotentiators and delivery systems for use in vaccines. Prog Microbiol Immunol. Dec. 31, 2012;(3):1-8.

Novokhatskiy et al., Problema kontaminatsii kletkami I novyie podkhody k kontroliu perevivaiemykh liniy. Voprosy virusologii. 1977;4:396-408.

Ogurtsov et al., Biotechnology. Principles and Application Training Manual. Ministry of Education and Science. 2012. 344 pages.

Paganin-Gioanni et al., Direct visualization at the single-cell level of siRNA electrotransfer into cancer cells. Proc Natl Acad Sci U S A. Jun. 28, 2011;108(26):10443-7. doi: 10.1073/pnas.1103519108. Epub Jun. 13, 2011.

Ramakrishnan et al., 1743-P: Engineering Erythrocytes with the SQZ Cell Therapy Platform to Enhance Immunotolerance. Diabetes. Jun. 2019;68(Supplement 1). https://doi.org/10.2337/db19-1743-P. Abstract.

Song et al., Scientific basis for the use of hypotonic solutions with ultrasonic liposuction. Aesthetic Plast Surg. Mar.-Apr. 2006;30(2):233-8. doi: 10.1007/s00266-005-0087-z.

Tran et al., Expansion of immature, nucleated red blood cells by transient low-dose methotrexate immune tolerance induction in mice. Clin Exp Immunol. Nov. 18, 2020;0:1-15. doi: 10.1111/cei.13552.

Vechkanov et al., Osnovy kletochnoy inzhenerii: Study guide. Rostov-on-Don. 2012; 133 pages. Relevant pp. 15-16.

Vinulan, SQZ Biotech Lines Up an IPO on the NYSE to Fund Cell Therapy R&D. Xconomy. Oct. 12, 2020. https://xconomy.com/boston/2020/10/12/sqz-biotech-lines-up-an-ipo-on-the-nyse-to-fund-cell-therapy-rd/ [last accessed Jan. 28, 2021]. 3 pages.

Wen et al., Shear Effects on Stability of DNA Complexes in the Presence of Serum. Biomacromolecules. Oct. 9, 2017;18(10):3252-3259. doi: 10.1021/acs.biomac.7b00900. Epub Sep. 1, 2017.

Yangulov et al., Vliyaniye razlichnykh kriozashchitnykh sred na zhiznesposobnost kriokonservirovannykh limfoblastnykh kletochnyk liniy H-9 I U-937. Problemy kriobiologii. 1991;3:46-9.

Ye, Complexation between milk proteins and polysaccharides via electrostatic interaction: principles and applications—a review. Int J Food Sci Technol. Jan. 31, 2008;43(3):406-15.

Zhdanov et al., Tayna tretiego tsarstva. Znaniye. 1975; 176 pages. Relevant pp. 124-125.

U.S. Appl. No. 17/404,286, filed Aug. 17, 2021, Sharei et al.

U.S. Appl. No. 17/394,125, filed Aug. 4, 2021, Sharei et al.

EP 21158382.8, Jun. 11, 2021, Extended European Search Report. Extended European Search Report for EP Application No. 21158382.8 dated Jun. 11, 2021.

Baumann et al., Hemolysis of human erythrocytes with saponin affects the membrane structure. Acta Histochem. Feb. 2000;102(1):21-35. doi: 10.1078/0065-1281-00534.

Berrington et al., Lymphocyte subsets in term and significantly preterm UK infants in the first year of life analysed by single platform flow cytometry. Clin Exp Immunol. May 2005;140(2):289-92. doi: 10.1111/j.1365-2249.2005.02767.x.

Carlson et al., Self-Sorting of White Blood Cells in a Lattice. PRL. Sep. 15, 1997;79(11):2149-52.

De Clercq, Antiviral drugs in current clinical use. J Clin Virol. Jun. 2004;30(2):115-33. doi: 10.1016/j.jcv.2004.02.009.

Hoffman, On Red Blood Cells, Hemolysis and Resealed Ghosts. In: The Use of Resealed Erythrocytes as Carriers and Bioreactors. 1992. Magnani et al.,. Eds. Chapter 1:1-15.

Johnson et al., Loss of resealing ability in erythrocyte membranes. Effect of divalent cations and spectrin release. Biochim Biophys Acta. May 4, 1978;509(1):58-66. doi: 10.1016/0005-2736(78)90007-x. Abstract only.

Kinosita Jr. et al., Survival of sucrose-loaded erythrocytes in the circulation. Nature. Mar. 16, 1978;272(5650):258-60. doi: 10.1038/272258a0.

Lee et al., Kinetic studies of human erythrocyte membrane resealing. Biochim Biophys Acta. Apr. 26, 1985;815(1):128-34. doi: 10.1016/0005-2736(85)90482-1. Abstract only.

Lizano et al., Mouse erythrocytes as carriers for coencapsulated alcohol and aldehyde dehydrogenase obtained by electroporation in vivo survival rate in circulation, organ distribution and ethanol degradation. Life Sci. Mar. 16, 2001;68(17):2001-16. doi: 10.1016/s0024-3205(01)00991-2.

McNeil et al., Coping with the inevitable: how cells repair a torn surface membrane. Nat Cell Biol. May 2001;3(5):E124-9. doi: 10.1038/35074652. Abstract only.

McNeil et al., Plasma membrane disruption: repair, prevention, adaptation. Annu Rev Cell Dev Biol. 2003;19:697-731. doi: 10.1146/annurev.cellbio.19.111301.140101.

McNeil et al., The endomembrane requirement for cell surface repair. Proc Natl Acad Sci U S A. Apr. 15, 2003;100(8):4592-7. doi: 10.1073/pnas.0736739100. Epub Apr. 2, 2003.

McNeil, Repairing a torn cell surface: make way, lysosomes to the rescue. J Cell Sci. Mar. 1, 2002;115(Pt 5):873-9.

Nagel et al., HbS-oman heterozygote: a new dominant sickle syndrome. Blood. Dec. 1, 1998;92(11):4375-82.

Razizadeh et al., Coarse-Grained Modeling of Pore Dynamics on the Red Blood Cell Membrane under Large Deformations. Biophys J. Aug. 4, 2020;119(3):471-482. doi: 10.1016/j.bpj.2020.06.016. Epub Jun. 24, 2020.

Reddy et al., Plasma membrane repair is mediated by Ca(2+)-regulated exocytosis of lysosomes. Cell. Jul. 27, 2001;106(2):157-69. doi: 10.1016/s0092-8674(01)00421-4.

Redman, Phospholipid metabolism in intact and modified erythrocyte membranes. J Cell Biol. Apr. 1971;49(1):35-49. doi: 10.1083/jcb.49.1.35.

Sachs, Potassium-potassium exchange as part of the over-all reaction mechanism of the sodium pump of the human red blood cell. J Physiol. May 1986;374:221-44. doi: 10.1113/jphysiol.1986.sp016076.

(56) References Cited

OTHER PUBLICATIONS

Salgado et al., Red blood cell membrane-facilitated release of nitrite-derived nitric oxide bioactivity. Biochemistry. Nov. 10, 2015;54(44):6712-23. doi: 10.1021/acs.biochem.5b00643. Epub Oct. 28, 2015. Abstract only.

Saulis, The loading of human erythrocytes with small molecules by electroporation. Cell Mol Biol Lett. 2005;10(1):23-35.

Schatzmann et al., Calcium movements across the membrane of human red cells. J Physiol. Apr. 1969;201(2):369-95. doi: 10.1113/jphysiol.1969.sp008761.

\* cited by examiner

DELIVERY OF MATERIALS TO ANUCLEATE CELLS

CROSS-REFERENCE TO RELATED APPLICATIONS

This application is a continuation of International Patent Application PCT/US2016/041653, filed Jul. 8, 2016, which claims priority to U.S. Provisional Application No. 62/190,677, filed, Jul. 9, 2015, the disclosures of which are incorporated by reference herein in their entireties.

STATEMENT AS TO FEDERALLY-SPONSORED RESEARCH

This invention was made with Government support under Grant Nos. R01 GM101420 and EB011187 awarded by the National Institutes of Health (NIH). The Government has certain rights in the invention.

TECHNICAL FIELD

The subject matter described herein relates to delivery of materials to anucleate cells, for example delivering macromolecules to red blood cell cytoplasm.

BACKGROUND

Adult humans have approximately 20-30 trillion red blood cells (RBCs) at a given time, amounting to approximately a quarter of the total number of cells in the human body and comprising 40-45% of total blood volume. RBCs are anucleate (e.g., lacking a nucleus) and have a half-life of approximately 127 days in circulation. This long half-life and relative abundance make RBCs an attractive candidate for novel therapeutics platforms. Modification of RBCs to provide clinically beneficial functions can allow them to be used to facilitate longitudinal therapeutic benefits. These therapeutic benefits are especially applicable in the context of therapies against intracellular parasites, such as those that cause malaria, and in the treatment of genetic defects affecting RBC function (e.g., sickle cell disease). The long half-life of RBCs can allow for the persistence of a drug or treatment for significantly longer than synthetic carriers and thus allows for prolonged, sustained release of the drug, as well as minimal injections or administrations. Red blood cells further have the capability to access most sites in the human body, potentially expanding the applications of existing treatment regimens that may be restricted to a specific administration route. Furthermore, due to the tolerogenic nature of red blood cells, the delivered material can be used to control the immune response.

However, the modification of red blood cells presents several challenges, as their unique structural and physiological properties make it difficult to deliver material into their cytoplasm. Conventional techniques such as electroporation and lipofection in isolation can be ineffective in these cell types due to a lack of repair mechanisms and endocytic pathways. Alternative methods using osmotic shock can kill or severely destabilize red blood cells, severely reducing the half-life of the red blood cell. As such, there is a need in the art for systems and methods that allow for the delivery of compounds to the cytosol of RBCs and other anucleate cells without a loss of cell viability or function.

The methods and systems described herein have overcome the barriers to penetration of RBCs while preserving the viability and function of these cells compared to other methods. Using a rapid deformation based microfluidic system, loading of red blood cells with macromolecules of different sizes has been shown. Although delivery to some mammalian cells, such as cancer cell lines and fibroblasts, has been previously demonstrated using this technique, the designs of those particular microfluidic systems were incompatible with RBCs, due to the dramatically different physical properties of the cell types being processed. Through the optimization of multiple parameters, including the use of one or more of smaller constriction sizes, high pressure, and different buffers, successful delivery of materials to RBCs was achieved. Moreover, the current subject matter is not material specific and can enable delivery of a diversity of materials, such as nucleic acids, proteins, small molecule drugs, to the cytosol of anucleate cells. By enabling robust delivery to RBCs in a simple, scalable manner, the current subject matter can be implemented in a diversity of applications that deliver material to study red blood cell diseases and facilitate the use red blood cells as a therapeutics platform.

BRIEF SUMMARY

Embodiments of the current invention are directed to a microfluidics system for causing perturbations in a cell membrane, the system comprising at least one microfluidics channel defining a lumen and being configured such that a cell suspended in a buffer can pass therethrough, wherein the microfluidics channel comprises at least one cell-deforming constriction comprising a length, a depth, and a width, wherein the wide of the constriction is less than 4 micrometers. In one embodiment of this aspect of the disclosure, said cell is anucleate. In one embodiment of this aspect of the disclosure, said cell is one or more of a red blood cell, an erythrocyte, a reticulocyte, or a platelet. In a further embodiment of this aspect of the disclosure, said cell suspended in a buffer comprises unmodified blood. In a further embodiment of this aspect of the disclosure, said cell is a healthy cell. In one embodiment of this aspect of the disclosure, said cell is a diseased or infected cell.

Certain embodiments of the present disclosure are directed to a microfluidics system described herein for causing perturbations in a cell membrane, the system comprising at least one microfluidics channel defining a lumen and being configured such that a cell suspended in a buffer can pass therethrough, wherein the microfluidics channel comprises at least one cell-deforming constriction comprising a length, a depth, and a width, wherein the wide of the constriction is less than 4 micrometers. In certain embodiments of this aspect of the disclosure, the width of the constriction is between 0.5 micrometers and 4 micrometers. In further embodiments of this aspect of the disclosure, the width of the constriction is between 3 micrometers and 4 micrometers. In a further embodiment of this aspect of the disclosure, the width of the constrictions is less than the largest diameter of the cell. In some embodiments of this aspect of the disclosure, the width is about 20% to about 99% of the largest diameter of the cell. In a further embodiment of this aspect of the disclosure, the length of the constrictions is 30 micrometers or less. In a further embodiment of this aspect of the disclosure, the length is between 10 micrometers and 30 micrometers. In certain embodiments of this aspect of the disclosure, the length of the constriction is between 10 micrometers and 20 micrometers. In a further embodiment of this aspect of the disclosure, the depth of constriction is between 1 μm and 1 mm. In a further embodiment, the depth of constriction is about 20 μm. In certain embodiments of this aspect of the disclosure, the depth of constriction and the width of constriction are equal.

Certain embodiments of the present disclosure are directed to a microfluidics system described herein for causing perturbations in a cell membrane, the system comprising at least one microfluidics channel defining a lumen and being configured such that a cell suspended in a buffer can pass therethrough, wherein the microfluidics channel comprises at least one cell-deforming constriction comprising a length, a depth, and a width, wherein the wide of the constriction is less than 4 micrometers. In certain embodiments of this aspect of the disclosure, the microfluidics system comprises multiple microfluidics channels. In a further embodiment of this aspect of the disclosure, the microfluidics system comprises multiple microfluidics channels arranged in parallel. In certain embodiments of this aspect of the disclosure, the microfluidics system comprises multiple cell-deforming constrictions. In a further embodiment of this aspect of the disclosure the microfluidics system comprises multiple cell-deforming constrictions arranged in series in the same microfluidics channel.

Certain embodiments of the present disclosure include a microfluidics system for causing perturbations in a cell membrane, the system comprising at least one microfluidics channel defining a lumen and being configured such that a cell suspended in a buffer can pass therethrough, wherein the microfluidics channel comprises at least one cell-deforming constriction comprising a length, a depth, and a width, wherein the wide of the constriction is less than 4 micrometers. Certain embodiments of this aspect of the disclosure include microfluidics systems further comprising a cell driver adapted to apply a pressure to the buffer for passing the cell suspended in the buffer through the cell-deforming constriction. In further embodiments of this aspect of the disclosure, the cell driver is adapted to apply a pressure greater than 90 psi to the buffer. In further embodiments of this aspect of the disclosure, the cell driver is adapted to apply a pressure of 120 psi. In still further embodiments of this aspect of the disclosure, the cell driver is selected from a group comprising a pressure pump, a gas cylinder, a compressor, a vacuum, a syringe, a syringe pump, a peristaltic pump, a pipette, a piston, a capillary actor, a human heart, human muscle, gravity, and a microfluidic pump.

Certain embodiments of the present disclosure include a microfluidics system for causing perturbations in a cell membrane, the system comprising at least one microfluidics channel defining a lumen and being configured such that a cell suspended in a buffer can pass therethrough, wherein the microfluidics channel comprises at least one cell-deforming constriction comprising a length, a depth, and a width, wherein the wide of the constriction is less than 4 micrometers. Further embodiments of this aspect of the disclosure include microfluidics systems wherein a cross-section of the channel is selected from the group consisting of circular, elliptical, an elongated slit, square, hexagonal, and triangular.

Certain embodiments of the present disclosure are directed to methods comprising passing a cell suspended in a buffer through a microfluidic channel that includes a cell-deforming constriction such that a pressure is applied to the cell causing perturbations of the cell large enough for a payload to pass through, wherein a width of the constriction is less than 4 micrometers and incubating the cell in a payload-containing solution for a predetermined time before or after the cell passes through the constriction. In a further embodiment of this aspect of the disclosure, the cell is a nucleate. In certain embodiments of this aspect of the disclosure, the cell is one or more of red blood cells, erythrocytes, reticulocytes, or platelets. In a further embodiment of this aspect of the disclosure, the cell suspended in a buffer includes unmodified blood. In certain embodiments of this aspect of the disclosure, the cell is a healthy cell. In certain embodiments of this aspect of the disclosure, the cell is an infected or diseased cell.

Certain embodiments of the present disclosure are directed to methods comprising passing a cell suspended in a buffer through a microfluidic channel that includes a cell-deforming constriction such that a pressure is applied to the cell causing perturbations of the cell large enough for a payload to pass through, wherein a width of the constriction is less than 4 micrometers and incubating the cell in a payload-containing solution for a predetermined time before or after the cell passes through the constriction. In a further embodiment of this aspect of the disclosure, the width of the constriction is between 0.5 micrometers and 4 micrometers. In a further embodiment of this aspect of the disclosure, the width of the constriction is between 3 micrometers and 4 micrometers. In certain embodiments of this aspect of the disclosure, the width of constriction is less than the largest diameter of the cell. In certain embodiments of this aspect of the disclosure, the width of constriction is about 20% to about 99% of the largest diameter of the cell.

Certain embodiments of the present disclosure are directed to methods comprising passing a cell suspended in a buffer through a microfluidic channel that includes a cell-deforming constriction such that a pressure is applied to the cell causing perturbations of the cell large enough for a payload to pass through, wherein a width of the constriction is less than 4 micrometers and incubating the cell in a payload-containing solution for a predetermined time before or after the cell passes through the constriction. In a further embodiment of this aspect of the disclosure, the pressure applied to the cell is greater than 90 psi. In a further embodiment of this aspect of the disclosure, the pressure applied to the cell is 120 psi. In certain embodiments of this aspect of the disclosure, the buffer is a hypotonic buffer than causes the cell to swell.

Certain embodiments of the present disclosure are directed to methods comprising passing a cell suspended in a buffer through a microfluidic channel that includes a cell-deforming constriction such that a pressure is applied to the cell causing perturbations of the cell large enough for a payload to pass through, wherein a width of the constriction is less than 4 micrometers and incubating the cell in a payload-containing solution for a predetermined time before or after the cell passes through the constriction. In a further embodiment of this aspect of the disclosure, the payload-containing solution comprises one or more or proteins, small molecules, nucleic acids, lipids, carbohydrates, macromolecules, vitamins, polymers, fluorescent dyes, fluorophores, carbon nanotubes, quantum dots, nanoparticles, or steroids. In a further embodiment of this aspect of the disclosure, the payload-containing solution comprises proteins or dextran polymers. In certain embodiments of this aspect of the disclosure, the payload-containing solution comprises proteins and dextran polymers. In a further embodiment of this aspect of the disclosure, the payload-containing solution comprises a small molecule or a protein. In certain embodiments of this aspect of the disclosure, the payload-containing solution comprises a small molecule and a protein. In a further embodiment, the payload-containing solution includes one or more of chloroquine, atovaquone-proguanil, artemether/lymefantrine, quinine sulfate, mefloquine, hydroxychloroquine, primaquine, quinidine, artesunate, artemisinin, sulfadoxine/pryimethamine, amodiaquine, sulfonamides, halofantrine, doxycycline, tetracycline, clindamycin, hydroxyurea, hydrea, vitamin E, L-glutamine, acyclovir, ganciclovir, valacyclovir, or penciclovir, tri-peptides or tetra-peptides.

Certain embodiments of the present disclosure are directed to methods comprising passing a cell suspended in a buffer through a microfluidic channel that includes a cell-deforming constriction such that a pressure is applied to the cell causing perturbations of the cell large enough for a payload to pass through, wherein a width of the constriction is less than 4 micrometers and incubating the cell in a payload-containing solution for a predetermined time before or after the cell passes through the constriction. In a further embodiment of this aspect of the disclosure, a cross section of the microfluidic channel is selected from the group consisting of circular, elliptical, an elongated slit, square, hexagonal, and triangular. In certain embodiments of this aspect of the disclosure, incubating the cell in a payload-containing solution comprises incubating the cell for 0.0001 second to 20 minutes.

Certain embodiments of the present disclosure are directed to a method of treating an infection or disease, comprising passing a cell suspended in a buffer through a microfluidic channel that includes a cell-deforming constriction such that a pressure is applied to the cell causing perturbations of the cell large enough for a payload to pass through, wherein a width of the constriction is less than 4 micrometers, incubating the cell in a payload-containing solution for a predetermined time before or after the cell passes through the constriction, waiting for a predetermined amount of time for the perturbations of the cell to close such that the payload is contained intracellularly, and administering the cell to a patient in need thereof. In a further embodiment of this aspect of the disclosure, the cell is anucleate. In certain embodiments of this aspect of the disclosure, the cell is one or more of red blood cells, erythrocytes, reticulocytes, or platelets. In a further embodiment of this aspect of the disclosure, the cell suspended in a buffer includes unmodified blood. In further embodiments, the cell is a healthy cell. In certain embodiments, the cell is a diseased or infected cell.

Certain embodiments of the present disclosure are directed to a method of treating an infection or disease, comprising passing a cell suspended in a buffer through a microfluidic channel that includes a cell-deforming constriction such that a pressure is applied to the cell causing perturbations of the cell large enough for a payload to pass through, wherein a width of the constriction is less than 4 micrometers, incubating the cell in a payload-containing solution for a predetermined time before or after the cell passes through the constriction, waiting for a predetermined amount of time for the perturbations of the cell to close such that the payload is contained intracellularly, and administering the cell to a patient in need thereof. In a further embodiment of this aspect of the disclosure, the width of the constriction is between 0.5 micrometers and 4 micrometers. In a further embodiment of this aspect of the disclosure, the width of the constriction is between 3 micrometers and 4 micrometers. In certain embodiments of this aspect of the disclosure, the width of constriction is less than the largest diameter of the cell. In certain embodiments of this aspect of the disclosure, the width of constriction is about 20% to about 99% of the largest diameter of the cell.

Certain embodiments of the present disclosure are directed to a method of treating an infection or disease, comprising passing a cell suspended in a buffer through a microfluidic channel that includes a cell-deforming constriction such that a pressure is applied to the cell causing perturbations of the cell large enough for a payload to pass through, wherein a width of the constriction is less than 4 micrometers, incubating the cell in a payload-containing solution for a predetermined time before or after the cell passes through the constriction, waiting for a predetermined amount of time for the perturbations of the cell to close such that the payload is contained intracellularly, and administering the cell to a patient in need thereof. In further embodiments of this aspect of the disclosure, the pressure applied to the cell is greater than 90 psi. In certain embodiments of this aspect of the disclosure, the pressure applied to the cell is 120 psi. In further embodiments of this aspect of the disclosure, the buffer is a hypotonic buffer that causes the cell to swell. In certain embodiments of this aspect of the disclosure, a cross-section of the microfluidic channel is selected from the group consisting of circular, elliptical, an elongated slit, square, hexagonal, and triangular. In further embodiments, incubating the cell in a payload-containing solution comprises incubating the cell for 0.0001 seconds to 20 minutes.

Certain embodiments of the present disclosure are directed to a method of treating an infection or disease, comprising passing a cell suspended in a buffer through a microfluidic channel that includes a cell-deforming constriction such that a pressure is applied to the cell causing perturbations of the cell large enough for a payload to pass through, wherein a width of the constriction is less than 4 micrometers, incubating the cell in a payload-containing solution for a predetermined time before or after the cell passes through the constriction, waiting for a predetermined amount of time for the perturbations of the cell to close such that the payload is contained intracellularly, and administering the cell to a patient in need thereof. In further embodiments, the payload-containing solution comprises one or more of one or more or proteins, small molecules, nucleic acids, lipids, carbohydrates, macromolecules, vitamins, polymers, fluorescent dyes, fluorophores, carbon nanotubes, quantum dots, nanoparticles, or steroids. In certain embodiments, the payload-containing solution comprises a small molecule or a protein. In certain embodiments, the payload-containing solution comprises a small molecule and a protein. In certain embodiments, the payload containing solution includes one or more of hydroxyurea, hydrea, vitamin E, L-glutamine, acyclovir, ganciclovir, valacyclovir, penciclovir, tri-peptides, or tetra-peptides. In certain embodiments of this aspect of the disclosure, the cell is a sickle-cell disease affected cell. In further embodiments, the payload-containing solution includes one or more of chloroquine, atovaquone-proguanil, artemether/lymefantrine, quinine sulfate, mefloquine, hydroxychloroquine, primaquine, quinidine, artesunate, artemisinin, sulfadoxine/pryimethamine, amodiaquine, sulfonamides, halofantrine, doxycycline, tetracycline, or clindamycin. In certain embodiments of this aspect of the disclosure, the cell is infected with a malaria causing parasite. In further embodiments, the malaria-causing parasite is *P. falciparum*.

Certain embodiments of the present disclosure are directed to a method of treating an infection or disease, comprising passing a cell suspended in a buffer through a microfluidic channel that includes a cell-deforming constriction such that a pressure is applied to the cell causing perturbations of the cell large enough for a payload to pass through, wherein a width of the constriction is less than 4 micrometers, incubating the cell in a payload-containing solution for a predetermined time before or after the cell passes through the constriction, waiting for a predetermined amount of time for the perturbations of the cell to close such that the payload is contained intracellularly, and administering the cell to a patient in need thereof. In certain embodiments, the patient in need thereof suffers from sickle cell disease. In certain embodiments, the patient in need thereof is infected with a malaria-causing parasite. In certain embodiments, the patient in need thereof is infected with *P. falciparum*.

The details of one or more variations of the subject matter described herein are set forth in the accompanying drawings and the description below. Other features and advantages of the subject matter described herein will be apparent from the description, drawings, and claims.

DESCRIPTION OF THE DRAWINGS

FIG. 2B illustrates another view of the microfluidic channel including a constriction with a length, a width, and a depth.

FIG. 3C shows Giemsa-stained film smears of RBC samples infected with a synchronized culture of *P. falciparum* parasites at various stages of parasite growth. Time point 1 (T1) reflects ring-stage parasites (<18 hours post-invasion), time point 2 reflects trophozoite-stage parasites (<T1+8 hours), time point 3 reflects trophozoite-stage parasites (T1+22 hours), and time point 4 schizont-stage parasites (T1+30 hours).

FIG. 4B shows a photo of *P. falciparum*-infected, untreated RBCs.

Like reference symbols in the various drawings indicate like elements.

DETAILED DESCRIPTION

Figure 1A:
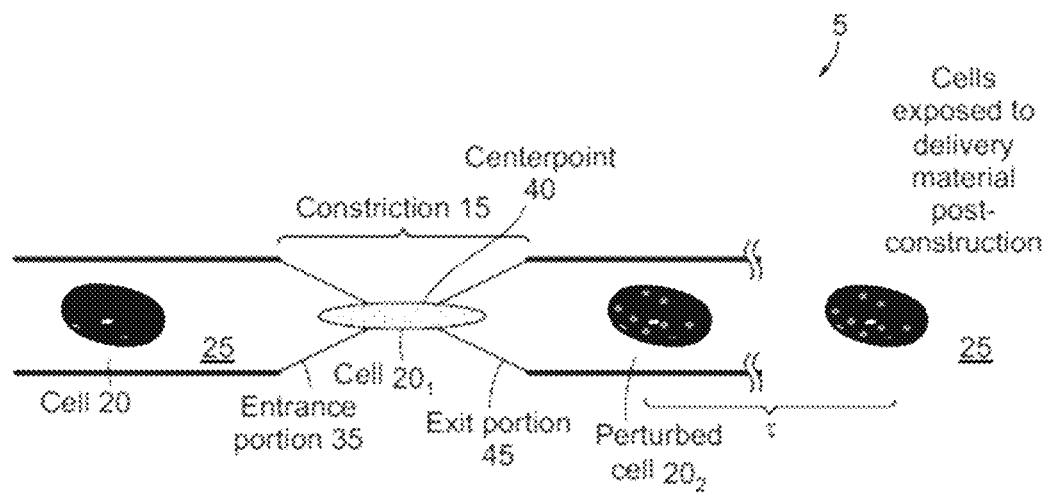
FIG. 1A and FIG. 1B illustrate an example of a microfluidic system (5) that can be used for the delivery of material, such as macromolecules, to anucleate cells, such as RBCs. Shown are the microfluidic system (5), including a channel defining a tubular lumen. The microfluidic channel includes a constriction (15) with a centerpoint (40), an entrance portion (35), and an exit portion (45). Also shown is a cell (20) suspended in a buffer (25), a cell passing through the constriction (15) (shown as $20_1$), a perturbed cell ($20_2$) and an amount of time the membrane remains disrupted after processing (τ). Also shown in FIG. 1B is the delivery material (30) and a delivered cell ($20_3$).

The subject matter described herein provides many technical advantages and can allow for the use of RBCs as a therapeutic platform. Red blood cells can be ideal drug carriers due to their long half-life in circulation (up to 127 days). However, red blood cells can be especially hard to manipulate due to the lack of active membrane recovery processes such as an inability to transcribe mRNA (Sharei et al., *Integr Biol (Camb)*. 2014 April; 6(4):470-475), a lack of other active processes such as endocytosis, as well as their flexible nature and bi concave shape. Example implementations of the current subject matter overcome these challenges in order to deliver materials to red blood cells by not relying on active endocytosis and through the use of unique combinations of conditions for the systems described herein. As such, the current invention is based at least in part on the unexpected finding that RBCs can restore perturbations in their membranes, despite a lack of active membrane repair processes.

The present disclosure relates to a microfluidics system capable of delivering materials to the cytosol of anucleate cells, such as RBCs, and methods of use. In particular embodiments, the microfluidics system comprises at least one microfluidic channel defining a lumen and being configured such that a cell suspended in a buffer can pass therethrough, wherein the microfluidic channel comprises at least one cell-deforming constriction comprising a width, a depth, and a length, wherein a width is less than 4 μm.

Embodiments of the invention also pertain to methods of delivering compounds and material (e.g., a payload or cargo) to the cytosol of an anucleate cell (e.g., a red blood cell), comprising passing an anucleate cell suspended in a buffer through a microfluidics channel described herein that includes a cell-deforming constriction such that a pressure is applied to the anucleate cell causing perturbations of the anucleate cell large enough for a payload to pass through, and incubating the anucleate cell in a payload-containing solution for an amount of time after the cell passes through the constriction to allow for the payload to enter into the cytosol of the anucleate cell. Further embodiments of the inventions are directed to methods of treating an infection or disease comprising passing an anucleate cell suspended in a buffer through a microfluidic device comprising a cell-deforming constriction and incubating the cell in a payload-containing solution for a predetermined amount of time, waiting for the perturbations to close such that the payload is contained intracellularly, and administering the cell to a patient in need. In still further embodiments said payload-containing solution includes a drug used in the treatment of malaria or sickle cell anemia.

Each embodiment in this specification is to be applied mutatis mutandis to every other embodiment unless expressly stated otherwise.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

As used in this specification and the appended claims, the singular forms "a," "an" and "the" include plural references unless the content clearly dictates otherwise.

As used in this specification, the term "and/or" is used in this disclosure to either "and" or "or" unless indicated otherwise.

The term "about" as used herein refers to the usual error range for the respective value readily known to the skilled person in this technical field. Reference to "about" a value or parameter herein includes (and describes) embodiments that are directed to that value or parameter per se.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

Microfluidics Systems and Devices

As used herein, "microfluidics systems" refers to systems in which low volumes (e.g., μL, nL, pL, fL) of fluids are processed to achieve the discrete treatment of small volumes of liquids. Certain implementations described herein include multiplexing, automation, and high throughput screening. The fluids (e.g., a buffer, a solution, a payload-containing solution, or a cell suspension) can be moved, mixed, separated, or otherwise processed. In certain embodiments described herein, microfluidics systems are used to apply mechanical constriction to a cell suspended in a buffer, inducing perturbations in the cell (e.g., holes) that allow a payload or compound to enter the cytosol of the cell.

As used herein, a "constriction" refers to a portion of a microfluidics channel defined by an entrance portion, a centerpoint, and an exit portion, wherein the centerpoint is defined by a width, a length, and a depth. As used herein, "width of constriction" refers to the width of the microfluidics channel at the centerpoint. In some embodiments, the constriction has a width of less than about 6 μm. For example, in some embodiments the constriction may be less than about 0.6 μm, 0.7 μm, 0.8 μm, 0.9 μm, 1 μm, 1.5 μm, or less than 2 μm. n some embodiments, the constriction has a width of less than about 4 μm. In certain aspects of the invention, the constriction has a width between about 0.51 μm and about 4 μm. In further embodiments, the constriction has a width between about 3 μm and 4 μm. In further embodiments, the constriction has a width between about 2 μm and 4 μm. In further aspects, the constriction has a width of about 3.9 μm or less. In further aspects, the constriction has a width of about 3 μm. In certain embodiments, the constriction is configured such that a single cell passes through the constriction at a time.

As used herein "length of constriction" refers to the length of the microfluidics channel at the centerpoint. In certain aspects of the invention, the length of the constriction is about 30 μm or less. In some embodiments, the length of the constriction is between about 10 μm and about 30 μm. In certain embodiments, the length of the constriction is between about 10 μm and about 20 μm. For example, the length of the constriction may be about 11 μm, 12 μm, 13 μm, 14 μm, 15 μm, 20 μm, or about 25 μm, including all integers, decimals, and fractions between 10 μm and 30 μm. The length of the constriction can vary to increase the length of time a cell is under constriction (e.g., greater lengths result in longer constrictions times at a given flow rate). The length of the constriction can vary to decrease the length of time a cell is under constriction (e.g., shorter lengths result in shorter constriction times at a given flow rate).

As used herein, "depth of constriction" refers to the depth of the microfluidics channel at the centerpoint. The depth of constriction can be adjusted to provide a tighter constriction and thereby enhance delivery, similar to adjustments of the constriction width. In some embodiments, the depth of the constriction is between about 1 μm and about 1 mm, including all integers, decimals, and fractions between 1 m and 1 mm. In some embodiments, the depth is about 20 μm. In some embodiments the depth is uniform throughout the channel. In certain embodiments, the depth is decreased at the point of constriction to result in a greater constriction of the cell. In some embodiments, the depth is increased at the point of constriction to result in a lesser constriction of the cell. In some embodiment, the depth of the constriction is greater than the width of the constriction. In certain embodiments, the depth of constriction is less than the width of the constriction. In some embodiments, the depth of constriction and the width of the constriction are equal.

As used herein, the dimensions of the microfluidic device are denoted by length, width, and number of constrictions. For example, a microfluidics device with a constriction length of 30 μm, a width of 5 μm, and 5 constrictions is represented herein as 30×5×5 (L×W×#of constrictions).

In some embodiments, the microfluidics system comprises at least one microfluidics channel comprising at least one constriction. In some embodiments, the microfluidics system comprises multiple microfluidics channels each comprising at least one constriction. For example, the microfluidics system may comprise 2, 3, 4, 5, 6, 7, 8, 9, 10, 50, 100, 500, 1000, or greater microfluidics channels, including all integers from 10 to 50, 50 to 100, 100 to 500, 500 to 1000, and the like. In certain aspects, the multiple microfluidics channels each comprising one constriction are arranged in parallel. In certain aspects, the multiple microfluidics channels each comprising one constriction are arranged linearly in series. In certain aspects of the invention, the microfluidics system comprises one microfluidics channel comprising multiple constrictions. For example, one microfluidics channel may comprise 2, 3, 4, 5, 10, 20, or greater constrictions. In some embodiments, the microfluidics system comprises multiple microfluidics channels comprising multiple constrictions. In some aspects of the invention, the multiple microfluidics channels comprising multiple constrictions are arranged in parallel. In some aspects of the invention, the multiple microfluidics channels comprising multiple constrictions are arranged linearly in series.

The entrance portion may comprise a "constriction angle" that can vary to increase or decrease how quickly the diameter of the channel decreases towards the centerpoint of the constriction. The constriction angle can vary to minimize clogging of the microfluidics system while cells are passing therethrough. For example, the constriction angle may be between 1 and 140 degrees. In certain embodiments, the constriction angle may be between 1 and 90 degrees. The exit portion may also comprise an angle to reduce the likelihood of turbulence/eddies that can result in non-laminar flow. For example, the angle of the exit portion may be between 1 and 140 degrees. In certain embodiments, the angle of the exit portion may be between 1 and 90 degrees.

The cross-section of the microfluidics channel, the entrance portion, the centerpoint, and the exit portion may vary. Non-limiting examples of various cross-sections include circular, elliptical, an elongated slit, square, hexagonal, or triangular cross-sections.

The velocity at which the anucleate cells (e.g., RBCs) pass through the microfluidics channels described herein can also be varied to control delivery of the delivery material to the cells. For example, adjusting the velocity of the cells through the microfluidics channel can vary the amount of time that pressure is applied to the cells, and can vary how rapidly the pressure is applied to the cell. In some embodiments, the cells can pass through the microfluidics system at a rate of at least 0.1 mm/s. In further embodiments, the cells can pass through the microfluidics system at a rate between 0.1 mm/s and 5 m/s, including all integers and decimals therein. In still further embodiments, the cells can pass through the microfluidics system at a rate between 10 mm/s and 500 mm/s, including all integers and decimals therein. In some embodiments, the cells can pass through the system at a rate greater than 5 m/s.

Cells are moved (e.g., pushed) through the microfluidics channels by application of pressure. In some embodiments, said pressure is applied by a cell driver. As used herein, a cell driver is a device or component that applies a pressure or force to the buffer or solution in order to drive a cell through a constriction. In some embodiments, a pressure can be applied by a cell driver at the inlet. In some embodiments, a vacuum pressure can be applied by a cell driver at the outlet. In certain embodiments, the cell driver is adapted to supply a pressure greater than 90 psi. For example, the pressure supplied by the cell driver can be greater than 91, 92, 93, 94, 95, 100, 110, 120, 130, or 150 psi. In further embodiments, the cell driver is adapted to apply a pressure of 120 psi. In certain embodiments, the cell driver is selected from a group consisting of a pressure pump, a gas cylinder, a compressor, a vacuum pump, a syringe pump, a peristaltic pump, a pipette, a piston, a capillary actor, a human heart, human muscle, gravity, a microfluidics pumps, and a syringe. Modifications to the pressure applied by the cell driver also affect the velocity at which the cells pass through the microfluidics channel (e.g., increases in the amount of pressure will result in increased cell velocities).

When a cell (e.g., an anucleate cell) passes through the constriction, its membrane is perturbed causing temporary disruptions in the membrane and resulting in the uptake of the payload that is present in the surrounding media. As used herein, these temporary disruptions are referred to as "perturbations." Perturbations created by the methods described herein are breaches in a cell that allow material from outside the cell to move into the cell. Non-limiting examples of perturbations include a hole, a tear, a cavity, an aperture, a pore, a break, a gap, or a perforation. The perturbations (e.g., pores or holes) created by the methods described herein are not formed as a result of assembly of protein subunits to form a multimeric pore structure such as that created by complement or bacterial hemolysins.

Anucleate Cells and Physiology

As used herein, "anucleate cells" refer to cells lacking a nucleus. Such cells can include, but are not limited to, platelets, red blood cells or erythrocytes (used interchangeably herein), and reticulocytes. Reticulocytes are immature (e.g., not yet biconcave) red blood cells, typically comprising about 1% of the red blood cells in the human body. Reticulocytes are also anucleate. In certain embodiments, the systems and methods described herein are used the treatment and/or processing of enriched (e.g., comprising a greater percentage of the total cellular population than would be found in nature), purified, or isolated (e.g. from their natural environment, in substantially pure or homogeneous form) populations of anucleate cells (e.g. RBCs, reticulocytes, and/or platelets). In certain embodiments, the systems and methods described herein are used the treatment and/or processing of whole blood containing RBCs, reticulocytes, platelets as well as other blood cells. Purification or enrichment of these cell types is accomplished using known methods such as density gradient systems (e.g., Ficoll-Hypaque), fluorescence activated cell sorting (FACS), magnetic cell sorting, or in vitro differentiation of erythroblasts and erythroid precursors.

Red blood cells comprise 40-45% of the total blood volume are structurally and functionally unique and are more flexible than cells with a nucleus. RBCs are the primary means for oxygen delivery throughout the human body, and the cytoplasm of an erythrocyte is rich in the oxygen-carrier biomolecule, hemoglobin. As such, RBCs lack most organelles (including a nucleus), which significantly alters their physical properties compared to enucleated cells. The biconcave shape of RBCs also contributes to their unique physical properties. RBCs are biconcave discs with an average disc thickness of 2-2.5 µm, and a minimum thickness in the center of 0.8-1 µm. This geometry provides extra surface area and enables shape change without increasing surface area.

The cell membranes of RBCs also play an important role in providing properties essential for physiological cell function (e.g., surface deformability stability, flexibility, adhesion, and immune recognition). In addition to the lipid bilayer found in cell membranes of almost all living organisms and viruses, RBCs also contain a carbohydrate-rich, glycoprotein-polysaccharide covering on their exterior, referred to as glycoalyx. This glycocalyx covering is only found in some bacteria, epithelial cells and RBCs. It is a porous layer that is resistant to penetration, and serves to protect against vascular thrombosis (e.g., atherothrombosis)

and other diseases. Within the RBC lipid bilayer, cholesterol is distributed evenly between the inner and outer leaflets, and five major phospholipids (phosphatidylcholine, sphingomyelin, phosphatidylethanolamine, phosphoinositol, phosphatidylserine) are asymmetrically distributed among the bilayer. This asymmetrical distribution of phospholipids is critical for cell integrity and function (e.g., exposure of a phospholipid potentiates adhesion of RBCs to vascular endothelial cells, therefore preventing normal transit through the microvasculature).

Thus, due to (1) a biconcave geometry, 2) a lack of nucleus or other organelles reducing resistance to deformation, (3) cytoplasmic viscosity reflecting high hemoglobin concentration, (4) a lack of active membrane repair processes and (5) a unique membrane composition, RBCs have a deformability phenomenon not present in any other cell of mammalian organisms. This phenomenon allows them to behave like elastic bodies and change their shape extensively, characteristics that change with age.

RBCs change rigidity as they age. Irreducible complexation of hemoglobin with spectrin is a prominent marker of the in vivo aging process for RBCs, and may be tightly correlated with increased RBC rigidity, decreased deformability, echinocytosis, and erythrophagocytosis (Aging and death signaling in mature red cells: from basic science to transfusion practice; Marianna H. Antonelou, Anastasios G. Kriebardis, and Issidora S. Papassiderr; Blood Transfus. 2010 June; 8 (Suppl 3): s39-s47).

The successful processing of RBCs by the microfluidics systems described herein was an unexpected experimental outcome. The systems introduce material to the cytosol of cells through the mechanical introduction of perturbations in the cell membrane, which allows the materials to pass through and remain intracellular after the restoration of cell membrane integrity. Thus, the successful processing of RBCs by the systems described herein, which depends on the successful repair of the cellular membrane, occurred in RBCs despite a lack of active membrane repair processes.

Processing Anucleate Cells for Delivery of Cargo

As described above, the shape of an RBC is distinct from other mammalian cells. As a consequence of their asymmetric, biconcave shape, RBCs have the potential to enter and pass through the constriction in different orientations. This property is not present in other cells, which have a more or less spherical shape when in suspension. This is an unexpected element from a delivery stand point. For example, RBCs progressing through the constriction of the microfluidics devices described herein at their widest dimension are more likely to have the cell membrane disrupted, while RBCs progressing through the constriction at their narrowest dimension are less likely to have the cell membrane disrupted. Thus, the range of the constriction dimensions of the microfluidics devices and systems described herein is lower than earlier configurations in order to overcome the difficulties in working with cells of such unique character and dimensions (e.g., anucleate and asymmetrical cells such as RBCs). In some embodiments, anucleate cells are processed with the microfluidics systems described herein in which the microfluidics channel comprises a constriction with a width of at least about 6 μm or less. For example, RBCs may be processed with a constriction width of about 1, 2, 3, 4, 5, or about 6 μm. In other embodiments, the constriction width is between 11 μm and 4 μm. In further embodiments, the constriction width is between 2 μm and 4 μm.

As used herein, a "buffer" refers to standard buffers or standard physiologically-compatible buffered solutions used to suspend the cells as they are processed. A buffer can be any buffer commonly used in the art including, but not limited to, maleic acid, phosphoric acid, citric acid, malic acid, formic acid, lactic acid, succinic acid, acetic acid, pivalic acid, phosphoric acid, L-histidine, MES, bis-tris, MOPSO, PIPES, imidazole, MOPS, BES, TES, HEPES, DIPSO, TAPSO, TEA, NaCl, KCl, $Na_2HPO_4$, $KH_2PO_4$, $Na_2CO_3$, or $NaHCO_3$. Non-limiting examples of buffered solutions include phosphate buffered saline (PBS), and media commonly used in cell culture such as RPMI, DMEM, or IMDM. In some embodiments, hypotonic and/or hypoosmolar buffers are advantageous as they cause RBCs to swell rendering them more receptive to being squeezed as they proceed through the device and be more susceptible to membrane poration using mechanical deformation.

Surfactants can also be added to a buffer in order to reduce clogging of the microfluidics channel during operation. Surfactants can include poloxamer, animal-derived serum, and albumin protein, among others.

In certain embodiment described herein, both normal RBCs and altered RBCs (e.g., diseased or infected) are effectively processed using the microfluidics systems described herein. "Normal" RBCs refer to healthy, unaltered RBCs such as those not affected by a genetic or non-genetic abnormality or not infected with a pathogen such as a virus, bacteria, or parasite. Normal RBCs can be obtained from healthy individuals, such as individuals not infected with a pathogen and not suffering from a disease. Normal RBCs can be obtained from ex vivo culture systems, in which the resultant RBC population is not infected with any pathogen and is not experimentally altered to mimic a disease state. "Altered" RBCs refer to infected or diseased RBCs. "Infected RBCs" can refer to an RBC or population of RBCs that are infected with a bacteria, virus, or parasite (e.g., *P. falciparum*). "Diseased RBCs" can refer to an RBC or population of RBCs affected by a genetic or non-genetic abnormality resulting in decreased RBC function, number, or viability (e.g. sickle cell anemia). Altered RBCs (e.g., infected or diseased RBCs) can be obtained from an individual suffering from an infection or disease. Altered RBCs can be obtained from ex vivo culture systems in which the resultant populations of RBCs is exposed to a pathogen (e.g. *P. falciparum*) or is experimentally altered to mimic a diseased state.

In certain embodiments, both normal (e.g. uninfected or non-diseased) RBCs and altered (e.g. infected or diseased) RBCs are successfully treated with the microfluidics systems described herein and cargo effectively delivered to both populations of RBCs. For example, RBCs infected with *P. falciparum* and RBCs uninfected with *P. falciparum* were successfully treated and the level of cargo delivery was comparable between the two populations. In certain embodiments, the level of cargo delivery is increased in normal RBCs compared to altered RBCs. In certain embodiments, the level of cargo delivery is decreased in normal RBCs compared to altered RBCs.

As used herein "payload" refers to the material that is being delivered to the anucleate cell (e.g. an RBC). "Payload", "cargo", "delivery material", and "compound" are used interchangeably herein. In some embodiments, a payload may refer to a protein, a small molecule, a nucleic acid (e.g. RNA and/or DNA), a lipid, a carbohydrate, a macromolecule, a vitamin, a polymer, fluorescent dyes and fluorophores, carbon nanotubes, quantum dots, nanoparticles, and steroids. In some embodiments, the payload may refer to a protein or small molecule drug. RBCs delivered with drug can act as long-term drug carriers in the body. In some embodiments, a protein or small molecule drug is delivered into malaria-causing parasite-infected cells (e.g. *P. falciparum* infected RBCs) to confer a clinical benefit to subjects suffering from malaria. In certain embodiments, small molecule drugs, e.g., purine-based antiviral agents (DeBellis et al., 2003, Blood Cells Mol. Dis. 31:286-290; hereby incorporated by reference), or peptides, e.g., tri- or tetra-peptides (Votano et al., 1977, Science 196:1216-1219; hereby incorporated by reference) are delivered to RBCs affected with sickle cell anemia in order to confer a clinical benefit to subjects suffering from sickle cell anemia.

In some embodiments, an infected cell refers to a cell infected with a parasite that causes malaria. Such parasites are found in the *Plasmodium* genus and can include *P. falciparum, P. vivax, P. ovale, P malariae*, and *P. knowlesi*. In further embodiments, an infected cell refers to a cell infected with *P. falciparum*. In some embodiments, a diseased cell refers to a cell (e.g. an anucleate cell) affected by anemias including iron-deficiency anemia aplastic anemia, thalassemia, and sickle cell anemia, polycythemia vera, and thrombocytopenias including idiopathic thrombocytopenic purpura. In further embodiments, a diseased cell refers to a cell affected by sickle cell anemia.

Non-limiting examples of drugs used in the treatment of malaria that can be delivered to RBCs infected with malaria-causing parasites (e.g. *P. falciparum* infected RBCs) include chloroquine (also known as Aralen™), atovaquone-proguanil (also known as Malarone®), artemether/lymefantrine (also known as Coartem®), quinine sulfate (also known as Qualaquin®, QM-260®, and Quinamm®), mefloquine (also known as Lariam®), hydroxychloroquine (also known as Plaquineil® Sulfate and Qunieprox®), primaquine, quinidine (also known as Quin-G®, Cardioquin®, Quinora®, Quinidex Extentabs®, quinidine gluconate ER (also known as Quinaglute Dura-Tabs®), Quin-Release®), artesunate, artemisinin, sulfadoxine/pryimethamine (also known as Fansidar®), amodiaquine, sulfonamides, and halofantrine (also known as Halfan®). RBCs infected with malaria-causing parasites (e.g. *P. falciparum* infected RBCs) can also be delivered with antibiotics such as doxycycline, tetracycline, and clindamycin.

In some embodiments, proteins and/or enzymes are delivered to RBCs for the treatment of sickle cell disease. Non-limiting examples of drugs used in the treatment of sickle cell disease (e.g. sickle cell anemia) that can be delivered to RBCs affected with sickle cell anemia include hydroxyurea, hydrea, vitamin E, droxia, Aqual Sol E® (vitamin E), L-glutamine, Aquavite E® (vitamin E), Gluta-Solve® (L-glutamine), Alpha E® (vitamin E), E-400 clear® (vitamin E), Nutr E Sol® (vitamin E), E-600® (vitamin E), E Gems® (vitamin E), Aqua E® (vitamin E), Aqua Gem E® (vitamin E), SYMPT-XG® (L-glutamine), Nutrestore® (L-glutamine powder for oral solution), purine-based antiviral agents including acyclovir, ganciclovir, valacyclovir, penciclovir, and tri- and tetra-peptides.

In some embodiments, a payload is delivered to a population of RBCs in order to treat a condition that does not necessarily affect the population of RBCs themselves. In such embodiments, RBCs can act as long term drug carriers, or "drug depots." As used herein, "drug depot" refers to a long-term circulating RBC population that has been processed by the microfluidics systems described herein and contains a payload, compound, or cargo that is slowly released throughout an organism. The population of RBCs comprising the drug depot can be infected and/or diseased, uninfected and/or non-diseased, or a combination of infected and/or diseased and uninfected and/or diseased. The half-life of an RBC is approximately 127 days. Therefore at least a portion of the population of drug-depot RBCs can persist for about 254 days. In some embodiments, the population of drug depot RBCs can be replenished at a predetermined time point during treatment. In some embodiments, the population of drug depot RBCs can be replenished more than once at predetermined time points during treatment. For example, drug depot RBCs can be replenished 2, 3, 4, 5, 6, 7, 8, 9, 10 or more times during treatment. In some embodiments, the number of RBCs to be used as a drug depot can be increased to increase to concentration of payload to be released overtime. In some embodiments, the concentration of payload delivered to the RBCs to be used as a drug depot can be increased in order to increase the concentration of payload to be released overtime. The drug-depot RBCs can be used for the treatment of numerous diseases or disorders, including but not limited to cancer In some embodiments, RBC drug depots can be used as the sole treatment for a disease or disorder. In some embodiments, RBC drug depots can be used in combination with a conventional therapy for a given disease or disorder. In some embodiments, RBC drug depots can be utilized as a maintenance therapy after the completion of conventional therapy for a given disease or disorder. In further embodiments, RBC drug depots can be utilized prior to the initiation of conventional therapy. In some embodiments, RBC drug depots can be utilized both prior to the initiation and after the completion of a conventional therapy for a given disease or disorder. In further embodiments, RBC drug depots can be utilized prior to the onset of a disease or disorder in order to prevent the onset of the disease or disorder.

As used herein, a "patient" includes any mammalian subject from which a sample can be acquired. In certain embodiments, the mammal is a human. The methods of the present disclosure can also be employed for the treatment of non-human primates (e.g. monkeys, baboons, and chimpanzees) mice, rats, bovines, horses, cats, dogs, pigs, rabbits, goats, deer, sheep, ferrets, gerbils, guinea pigs, hamsters, bats, birds (e.g., chickens, turkeys, and ducks), fish and reptiles. As used herein, a "patient in need thereof" is a patient suffering from a disease or infection, including but not limited to cancer.

In some embodiments, cells are incubated in a payload-containing solution or buffer for a period of time after undergoing processing with the microfluidics systems described herein. For example, cells can be incubated in a payload-containing solution or buffer for 1 to 10 minutes or longer. As such, the incubation time period can be 2, 3, 4, 5, 6, 7, 8, or 9 minutes (or any decimal thereof) or longer. In some embodiments, the incubation time period is 15, 20, 30, 60 minutes or longer. In certain embodiments, cells are incubated in a payload-containing solution or buffer for a period of time before undergoing processing with the microfluidics systems described herein. In certain embodiments, cells are processed as described herein while in a payload-containing solution or buffer.

The devices, technologies, and methods described herein are implemented ex vivo, for example in a laboratory, centralized manufacturing facility, or cell-processing facility. In further embodiments, the devices, technologies, and methods are used as a bedside system in which patient samples, e.g., blood samples, or fractionated blood cell populations, are processed using a microfluidic device described herein, or a syringe adapted to include a constriction of appropriate size to deliver molecules to patient cells (e.g., RBCs). Such a system is analogous to a bedside dialysis system.

EXAMPLES

Figure 1B:
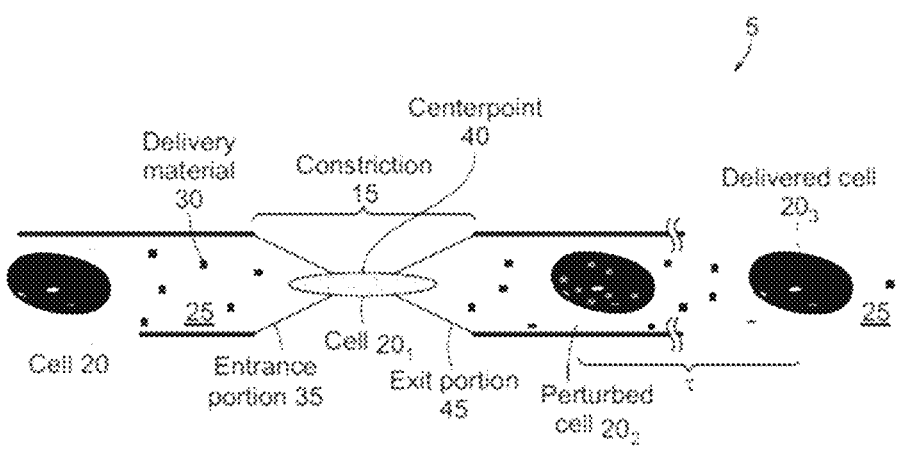

Example 1: Optimization of Microfluidic Systems for Delivery of Materials to Anucleate Cells Microfluidic systems capable of delivering a variety of compounds to anucleate cells were constructed. As described below, these microfluidic systems were constructed to allow for the passage of an anucleate cell suspended in a buffer through a constriction configured to cause perturbations in the cell large enough for a payload (e.g., compound or macromolecule) to pass through the cellular membrane and into the cytosol, resulting in a delivered cell. As shown in FIG. 1A and FIG. 1B, the microfluidic system (5) includes a channel that defines a tubular lumen. The microfluidic channel includes a constriction (15) that can be configured such that only a single cell (20) can pass through the constriction at one time. The cell can pass through the channel suspended in a buffer (25) that also includes delivery materials (30), although the delivery materials can be added to the buffer before or after the cells pass through the constriction. As the cell approaches and passes through the constriction, the constriction applies pressure (e.g., mechanical compression) to the cell, thereby squeezing the cell (shown as cell $20_1$). The pressure applied to the cell by the constriction causes perturbations (e.g., holes) in the cell membrane, resulting in a perturbed cell ($20_2$). Once the cell passes through the constriction, the perturbed cell begins to take up material in the buffer through the perturbations, including the delivery material, resulting in a delivered cell ($20_3$). The cell membrane recovers over time, and at least a portion of the delivery material remains trapped inside the cell.

Figure 2A:
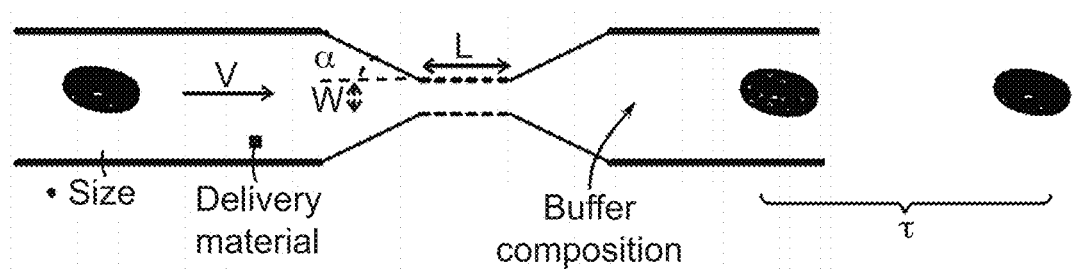
FIG. 2A and FIG. 2B illustrate an example of a microfluidic system that can be used for the delivery of materials, such as macromolecules, to anucleate cells, such as RBCs. Shown in FIG. 2A is a microfluidic channel including a constriction with a length (L) and a width (W), and an entrance portion including an angle of constriction (α). Also shown is an amount of time the membrane remains disrupted after processing (τ), and delivery material (square).
Figure 2B:
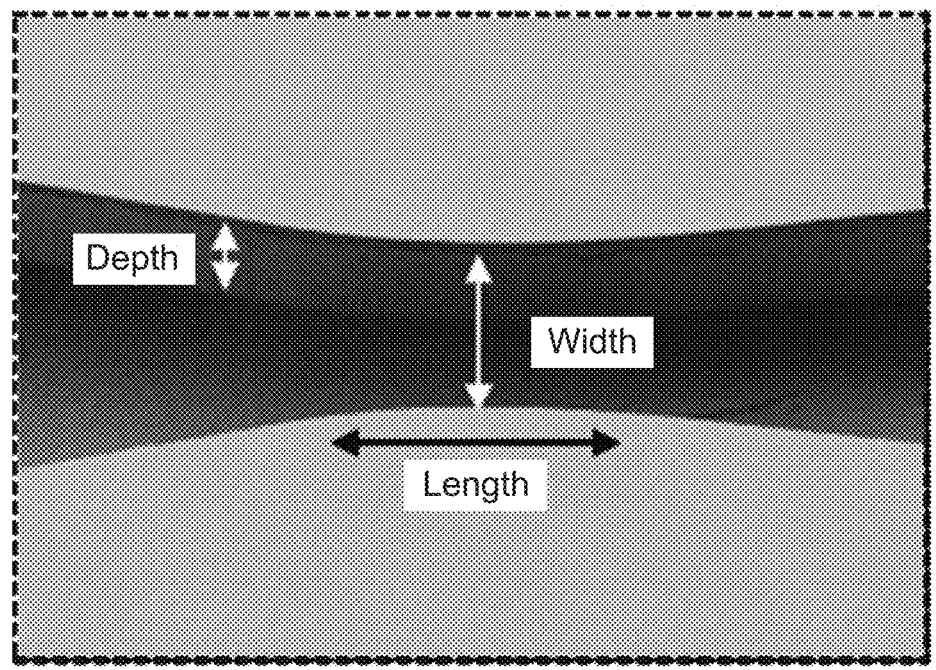

The ability of the microfluidic system to deform anucleate cells (e.g. RBCs) in order to deliver materials to the cytosol was optimized through modulation of parameters that define the centerpoint of the constriction (e.g. width, length, and depth), the pressure applied to the buffer to force the cell through the constriction, and the nature of the buffer. As illustrated in FIG. 2A-2B, the constriction includes an entrance portion, a centerpoint, and an exit portion. The centerpoint of constriction is defined by three measurements; a length (L), a width (W), and a depth. Optimal delivery of materials to RBCs required a width of less than 4 μm. Further, a pressure in excess of 90 pounds/inch$^2$ (psi) (e.g. 120 psi) resulted in perturbations sufficient for a payload to pass through the cell membrane and into the cytosol. One challenge of utilizing mechanical constriction to deliver material to RBCs is their asymmetric, bi-concave shape. This shape results in RBCs having a narrow dimension and a wide dimension, while many other cells have a relatively spherical shape while in suspension. Consequently, RBCs in a homeostatic state could pass through the constriction in different orientations, potentially reducing the efficacy of the microfluidic system. This challenge can be overcome through the use of a hypotonic buffer (e.g. PBS) which causes the RBCs to swell and exist in a more spherical shape. The use of hypotonic buffers can mitigate the effects of an RBC's asymmetric shape on the efficacy of the microfluidics systems described herein. Additionally, arrangement of multiple microfluidics channels and constriction in series or in parallel allowed for the development of microfluidics systems described herein that can deliver materials to RBCs.

Example 2: Delivery of Material to RBCs

Figure 3A:
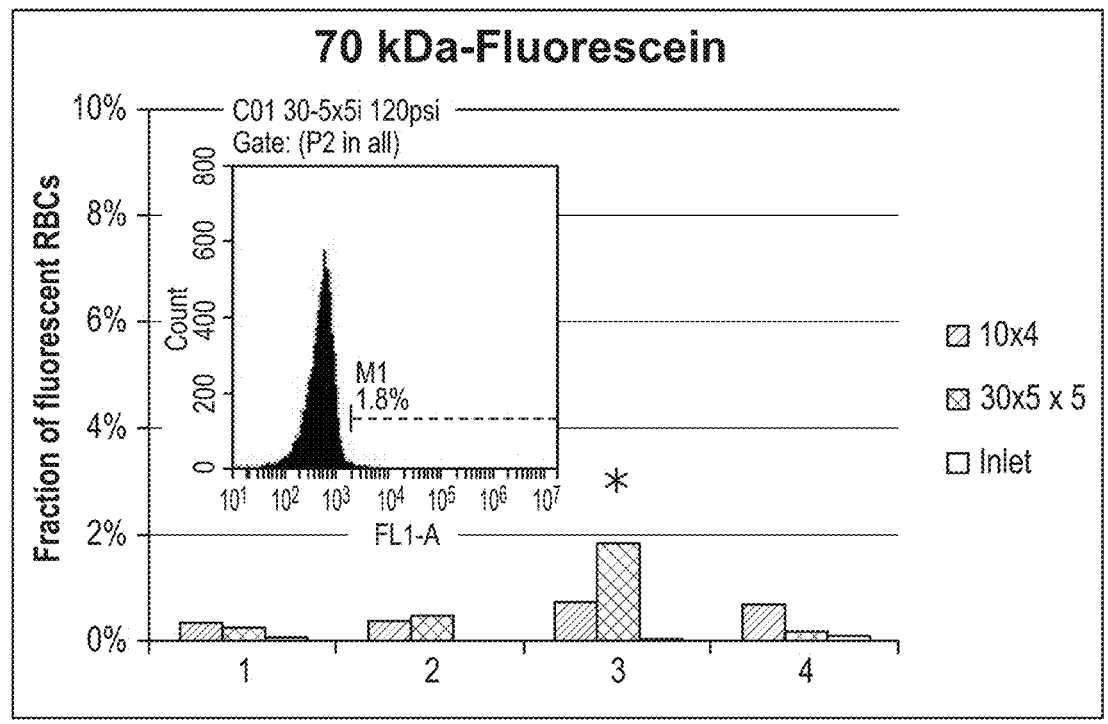
FIG. 3A-FIG. 3C show a series of plots illustrating delivery of materials to RBCs using example microfluidic systems and a series of images of red blood cells during delivery of materials to RBCs. 70 kDa dextran-fluorescein (FIG. 3A) and 10 kDa dextran-allophycocyanin (APC, FIG. 3B) were delivered using one of two device designs; one with a 10 μm length-4 μm width single constriction (10 μm×4 μm), and another with a 30 μm length-5 μm width constriction, with 5 constrictions in parallel (30 μm×5 μm,× 5). Histogram inserts in FIG. 3A and FIG. 3B show the delivered population (M1, FIG. 3A and M7, FIG. 3B) compared to the undelivered population.
Figure 3B:
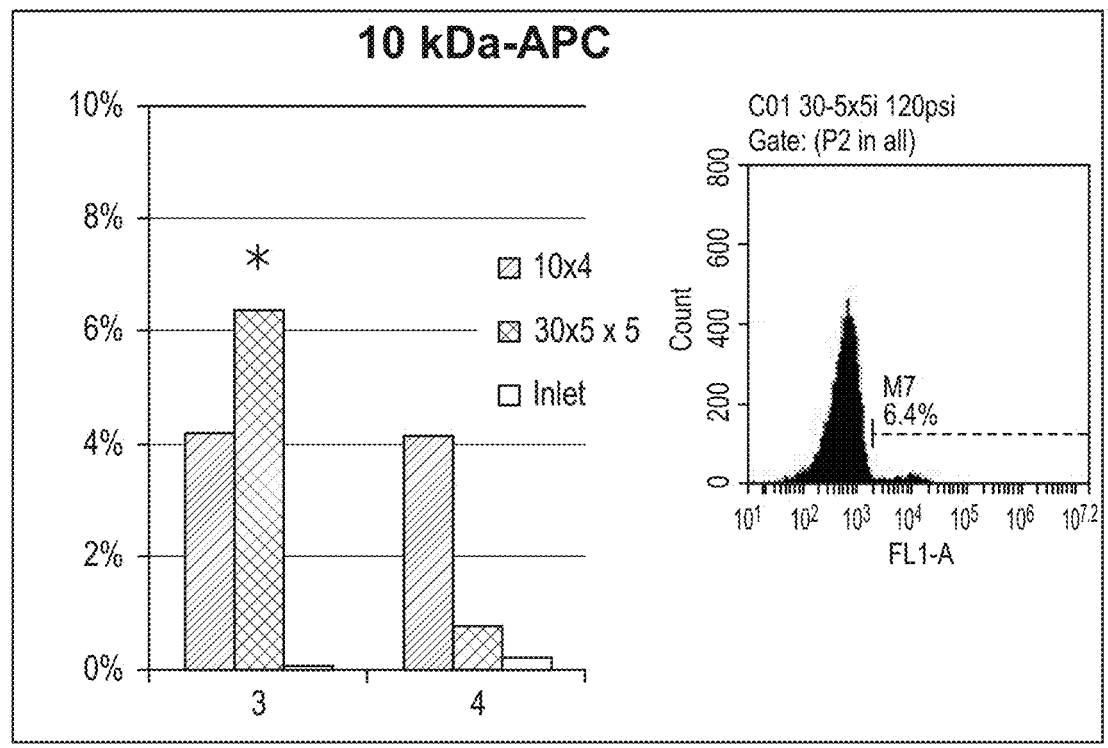
Figure 3C:
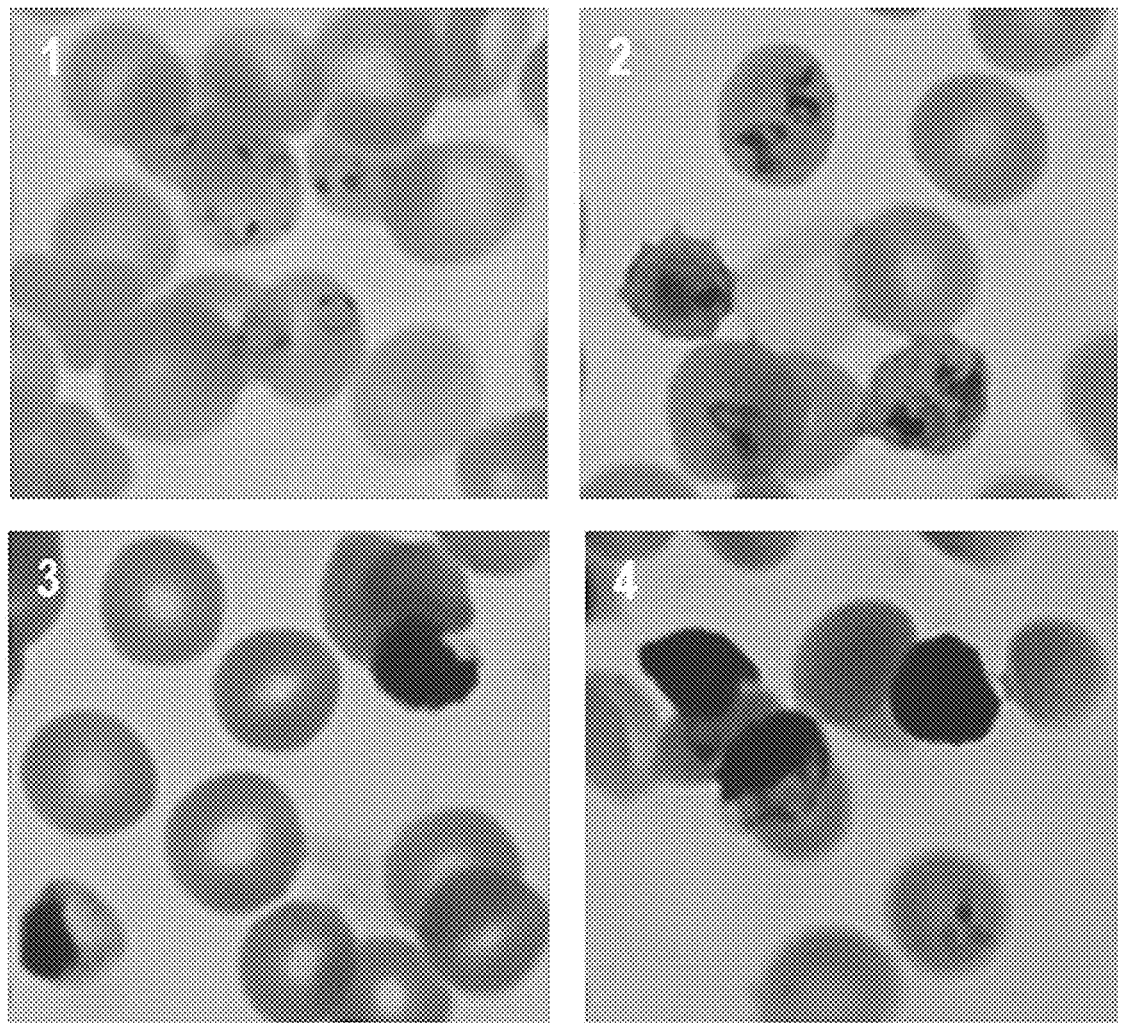

The ability of the microfluidics devices described herein to deliver material to human RBCs was tested using fluorescently labeled dextran polymers and fluorescent fusion proteins. Briefly, human RBCs were isolated from fresh blood and cultured in whole growth media. RBCs were infected with *P. falciparum*. Cells were harvested at four different time points post-infection. FIG. 3C shows thin film smears of red blood cell samples stained with Giemsa, highlighting the malarial parasites at various growth stages. Time point 1 reflects ring-stage parasites (<18 hours post-invasion), time point 2 reflects trophozoite-stage parasites (<T1+8 hours), time point 3 reflects trophozoite-stage parasites (T1+22 hours), and time point 4 schizont-stage parasites (T1+30 hours). RBCs at different stages of infection were harvested at the indicated time points and suspended in PBS at a density of 1×10$^8$ cells/mL. A given sample exposed to *P. falciparum* had both infected and uninfected cells. 70 kDa fluorescein-labeled dextran or 10 kDa APC-labeled dextran was delivered to the suspensions of infected and uninfected RBCs using microfluidics systems with one of two designs. One microfluidics system design comprised a single constriction with a length of 10 μm and a width of 4 μm (10×4). The other microfluidics system design comprised 5 constrictions arranged in parallel, each with a length of 30 μm and a width of 5 μm (30×5×5).

The ability of each microfluidics design to load 70 kDa FITC-labeled dextran (FIG. 3A) or 10 kDa APC-labeled dextran (FIG. 3B) into a mixed population of uninfected, enucleated red blood cells and infected, enucleated red blood cells at growth time points 1-4, was measured by flow cytometry. In each experiment, inlet cells (cells that had not passed through the constriction but had been exposed to the fluorescent delivery materials) were analyzed as negative controls for passive uptake of material. The histograms included in FIG. 3A and FIG. 3B illustrate the appearance of a delivered population relative to the undelivered group. The larger histogram peaks represent the undelivered population while the smaller peaks with higher fluorescence intensity represent the delivered population.

Loading of both the 70 kDa dextran-fluorescein conjugate (FIG. 3A) and 10 kDa dextran-APC conjugate (FIG. 3B) was maximal with a 30×5×5 channel geometry with parasites at the trophozoite-stage (time point 3). Delivery of 10 kDa dextran-APC resulted in a greater percentage of delivered RBCs than delivery of 70 kDa dextran-fluorescein, likely due to the smaller size of the delivery material. The ability of these microfluidics systems to successfully deliver material to RBC was an unexpected experimental outcome. RBCs are known to lack active membrane repair processes that would aid the closing of the induced perturbations and restoration of membrane integrity. However, the delivery of material to the cytosol of RBCs was successful in the absence of these active processes.

Figure 4A:
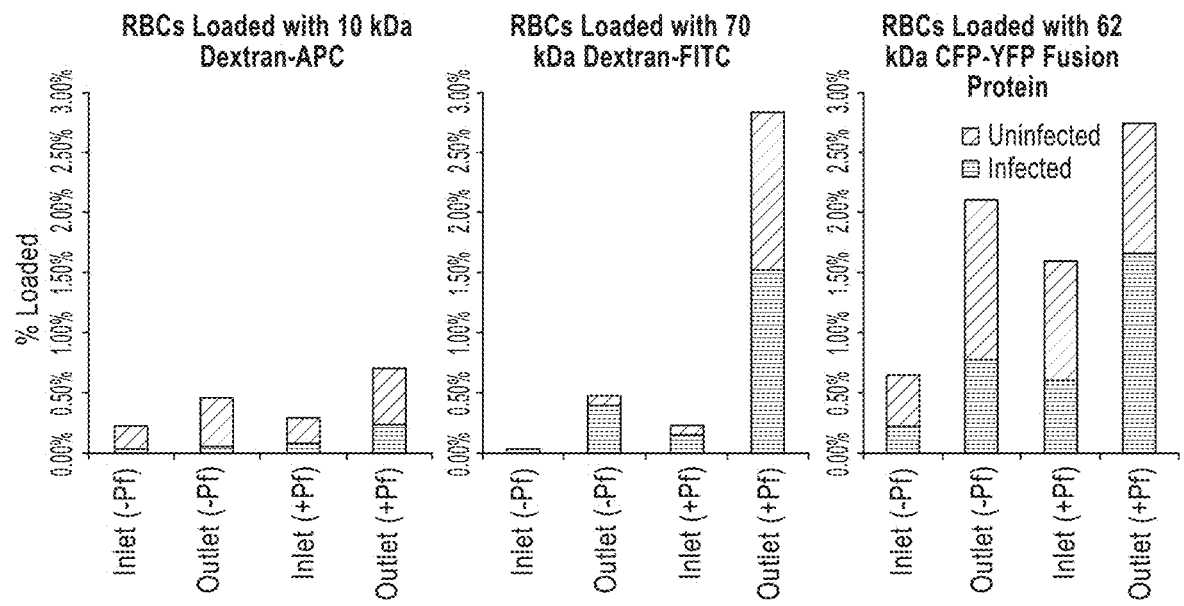
FIG. 4A-FIG. 4B illustrate delivery of 10 kDa Dextran-APC (FIG. 4A, left panel), 70 kDa Dextran-fluorescein (FIG. 4A, middle panel) and a recombinant cyan fusion protein (CFP)—yellow fusion protein (YFP) fusion (62 kDa CFP-YFP fusion) (FIG. 4A, right panel), to RBCs infected (top portion of bar graphs) or uninfected (bottom portion of bar graphs) with trophozoite-stage *P. falciparum* parasites using a microfluidic device with a 30 m×5 μm,×5 design.
Figure 4B:
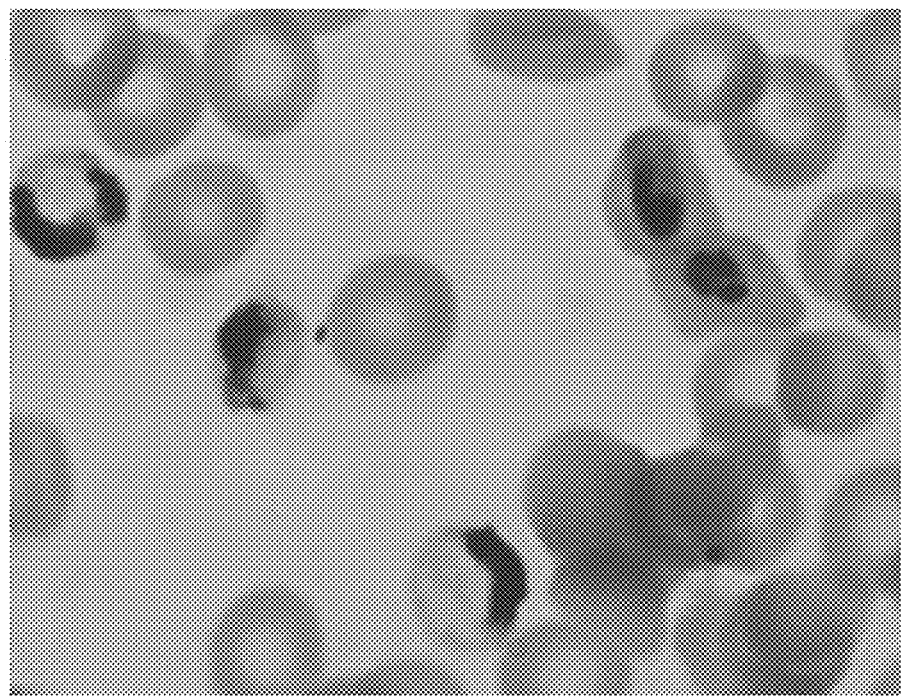
Figure 5A:
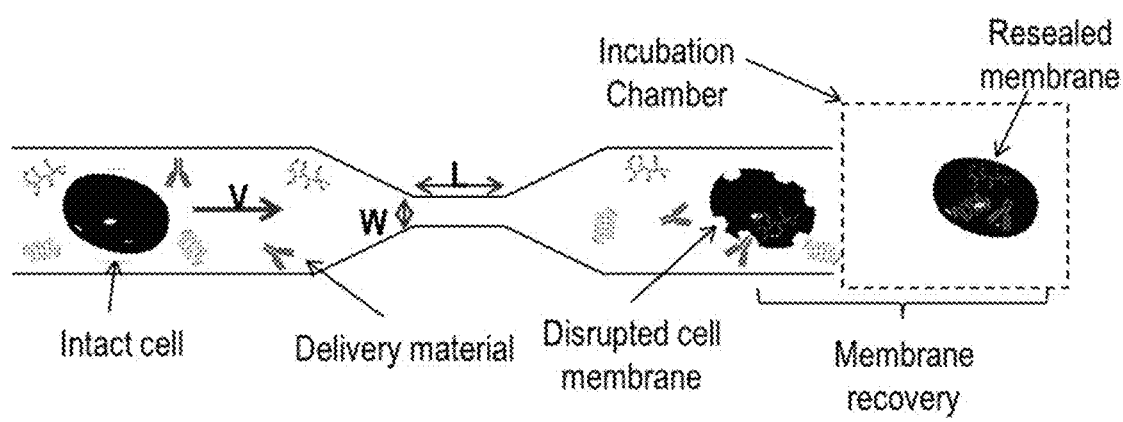
FIG. 5A-FIG. 5B. illustrate the example microfluidic system described and shown in FIG. 1A-FIG. 1B and FIG. 2A-FIG. 2B (FIG. 5A), and example delivery materials including lipids, polymers, nanoparticles, RNA, DNA, antibodies, proteins, impermeable small molecules, and fluorophores (FIG. 5B).
Figure 5B:
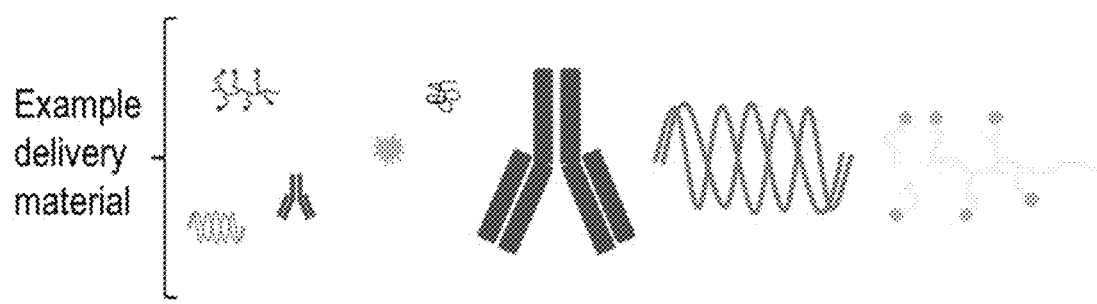

The conditions identified above (trophozoite-stage parasites and 30×5×5 geometry) were used to measure loading of the APC and fluorescein dextran conjugates and a 62 kDa recombinant protein, cyan fusion protein (CFP)—yellow fusion protein (YFP) fusion (CFP-YFP fusion) into parasitized vs. non-parasitized RBCs. The CFP-YFP fusion protein is charged, globular, and has a defined 3-dimensional structure representative of numerous proteins that can be delivered to confer clinical benefit and was thus used to mimic delivery of a physiologically-relevant protein. RBCs were infected with malaria and cells were harvested at the trophozoite-stage of growth for analysis. The experimental group infected with *P. falciparum* (+Pf) comprised both infected and uninfected RBCs. A separate group that was not exposed to *P. falciparum* was used as a negative control (−Pf). FIG. 4B is a stained picture of *P. falciparum*-infected cells. These data demonstrate successful delivery of materials of various physical characteristics (e.g., size, 3-D structure, and charge), and further indicate that both infected and uninfected RBCs can be successfully treated and cargo delivered using the microfluidics systems described herein. This result was surprising in light of the fact that parasite infection of RBCs (and replication of the parasite in the cells) renders the infected cells less flexible compared to uninfected cells. These data also indicate that the above described microfluidics devices and systems can be used to deliver a broad range of materials including lipids, polymers, nanoparticles, RNA, DNA, antibodies, proteins, impermeable small molecules, and fluorophores as shown in FIG. 5.

The subject matter described herein can be embodied in systems, apparatus, methods, and/or articles depending on the desired configuration. The implementations set forth in the foregoing description do not represent all implementations consistent with the subject matter described herein. Instead, they are merely examples consistent with aspects related to the described subject matter. Although a few variations have been described in detail above, other modifications or additions are possible including modifying the constriction design, angle of incidence of the cells entering the constriction, depth of constriction, choice of RBC stage and age, buffer, cell orientation, speed, temperature, presence of membrane stabilizing/destabilizing reagents (such as cholesterol and pluronics), and the like. The current subject matter is not limited to a laboratory or centralized manufacturing facility but also can be implemented as a bedside system, which can process patient samples in line, similar to a dialysis machine. A syringe type implementation can be possible. The current subject matter can be used on RBCs (including erythrocytes and reticulocytes), purified RBCs, and unmodified blood (e.g., blood that has undergone limited processing).

Other implementations are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

The invention claimed is:

1. A method for delivering a payload into a mammalian anucleate cell comprising:
passing the anucleate cell suspended in a buffer through a microfluidic channel that includes a cell-deforming constriction, wherein the step of passing the anucleate cell through the constriction causes perturbations of the membrane of the anucleate cell large enough for the payload to pass through, wherein the constriction comprises a width, a length and a depth, wherein the width of the constriction is less than 4 micrometers;
incubating the anucleate cell in a solution comprising the payload for a predetermined time before or after the anucleate cell passes through the constriction; and
delivering the payload into the anucleate cell.

2. The method of claim 1, wherein said cell is one or more of red blood cells, reticulocytes, and platelets.

3. The method of claim 2, wherein said cell is a red blood cell.

4. The method of claim 1, wherein said cell is a healthy cell.

5. The method of claim 4, wherein said cell is a red blood cell.

6. The method of claim 1, wherein said cell is an infected cell or a diseased cell.

7. The method of claim 6, wherein said cell is a red blood cell.

8. The method of claim 1, wherein the cell suspended in a buffer includes unmodified blood.

9. The method of claim 1, wherein the width of the constriction is between 0.5 micrometer and 4 micrometers.

10. The method of claim 9, wherein the width of the constriction is between 1 micrometer and 3 micrometers.

11. The method of claim 9, wherein said cell is a red blood cell.

12. The method of claim 9, wherein the width of the constriction is between 2 micrometers and 3 micrometers.

13. The method of claim 12, wherein said cell is a red blood cell.

14. The method of claim 9, wherein the width of the constriction is less than the largest diameter of the cell.

15. The method of any one of claim 9, wherein the width of the constriction is about 20% to about 99% the largest diameter of the cell.

16. The method of claim 1, wherein said buffer is a hypotonic buffer that causes said cell to swell.

17. The method of claim 1, wherein said payload-containing solution comprises one or more of proteins, peptides, small molecules, nucleic acids, lipids, carbohydrates, macromolecules, vitamins, polymers, fluorescent dyes, fluorophores, carbon nanotubes, quantum dots, nanoparticles, dextran polymers, and steroids.

18. The method of claim 1, wherein a cross-section of the microfluidic channel is selected from the group consisting of circular, elliptical, an elongated slit, square, hexagonal, and triangular.

19. The method of claim 1, wherein incubating the cell in a payload-containing solution comprises incubating the cell for 0.0001 seconds to 60 minutes.

20. The method of claim 1, wherein said length of the constriction is 30 micrometers or less.

21. The method of claim 1, wherein said depth of the constriction is between 1 micrometer and 1 millimeter.

22. The method of claim 1, wherein the microfluidic channel comprises a plurality of constrictions.

23. The method of claim 22, wherein the plurality of constrictions is arranged in series and/or parallel.

24. The method of claim 23, wherein the plurality of constrictions is arranged in parallel.

25. The method of claim 1, wherein the length of the constriction is between 10 micrometers and 30 micrometers.

26. The method of claim 1, wherein the length of the constriction is between 10 micrometers and 20 micrometers.

27. The method of claim 1, wherein said payload includes one or more of atovaquone-proguanil, artemether/lumefantrine, quinine sulfate, mefloquine, hydroxychloroquine, quinidine, sulfadoxine/pyrimethamine, amodiaquine, sulfonamides, halofantrine, doxycycline, tetracycline, hydrea, acyclovir, ganciclovir, valacyclovir, or penciclovir.

* * * * *